(12) United States Patent
Minnelli et al.

(10) Patent No.: US 11,376,063 B2
(45) Date of Patent: Jul. 5, 2022

(54) MONOPOLAR AND BIPOLAR FUNCTIONALITY

(71) Applicant: Ethicon LLC, Guaynabo, PR (US)

(72) Inventors: Patrick J. Minnelli, Harrison, OH (US); Darcy Greep, Cincinnati, OH (US); Ion Nicolaescu, Cincinnati, OH (US); John Brady, Cincinnati, OH (US); Chad Frampton, American Fork, UT (US); Matthew Schneider, Blue Ash, OH (US); Richard W. Timm, Cincinnati, OH (US); Mark Glassett, Madisonville, LA (US)

(73) Assignee: Cilag GmbH International, Zug (CH)

( * ) Notice: Subject to any disclaimer, the term of this patent is extended or adjusted under 35 U.S.C. 154(b) by 302 days.

(21) Appl. No.: 16/375,492

(22) Filed: Apr. 4, 2019

(65) Prior Publication Data

US 2020/0315691 A1   Oct. 8, 2020

(51) Int. Cl.
  *A61B 18/14*  (2006.01)
  *A61B 18/12*  (2006.01)
  *A61B 18/00*  (2006.01)

(52) U.S. Cl.
  CPC ...... *A61B 18/1445* (2013.01); *A61B 18/1206* (2013.01); *A61B 2018/0063* (2013.01);
  (Continued)

(58) Field of Classification Search
  CPC ............ A61B 18/1445; A61B 18/1206; A61B 2018/00601; A61B 2018/1253; A61B 2018/126; A61B 2018/00196; A61B 2018/1422; A61B 2018/1482; A61B 18/085; A61B 18/1442;
  (Continued)

(56) References Cited

U.S. PATENT DOCUMENTS

| 7,112,201 B2 | 9/2006 | Truckai et al. |
| 7,169,145 B2 | 1/2007 | Isaacson et al. |

(Continued)

FOREIGN PATENT DOCUMENTS

AU   2016228283 A1   10/2016

OTHER PUBLICATIONS

International Preliminary Report On Patentability received for PCT/IB2020/052712, dated Oct. 14, 2021, 10 pages.
(Continued)

*Primary Examiner* — Thomas A Giuliani
(74) *Attorney, Agent, or Firm* — Mintz Levin Cohn Ferris Glovsky and Popeo, P.C.

(57) ABSTRACT

Surgical devices, systems, and methods are provided for applying monopolar energy and bipolar energy to tissue. In one embodiment, a surgical device is provided with an end effector that has first and second jaws movable between an open position and a closed position, and a conductive member that extends through the end effector. The conductive member has a retracted position in which the conductive member is substantially disposed within the end effector and an extended position in which the conductive member extends at least partially distally beyond the end effector. The conductive member is configured to conduct energy through tissue adjacent thereto at least when the conductive member is in the extended position.

8 Claims, 18 Drawing Sheets

(52) U.S. Cl.
CPC ............... *A61B 2018/00589* (2013.01); *A61B 2018/00601* (2013.01); *A61B 2018/126* (2013.01); *A61B 2018/1253* (2013.01)

(58) Field of Classification Search
CPC .. A61B 2018/00589; A61B 2018/0063; A61B 2018/00607; A61B 2018/1455; A61B 2018/00595
USPC ............................................... 606/41, 50–52
See application file for complete search history.

(56) References Cited

U.S. PATENT DOCUMENTS

| | | | |
|---|---|---|---|
| 7,232,440 B2* | 6/2007 | Dumbauld | A61B 18/1445 606/51 |
| 7,416,101 B2 | 8/2008 | Shelton, IV et al. | |
| 9,675,405 B2 | 6/2017 | Trees et al. | |
| 10,010,309 B2 | 7/2018 | Bingham | |
| 10,010,366 B2 | 7/2018 | Strobl | |
| 2005/0113827 A1 | 5/2005 | Dumbauld et al. | |
| 2009/0202387 A1 | 8/2009 | Dlugos, Jr. et al. | |
| 2014/0005666 A1* | 1/2014 | Moua | A61B 18/1206 606/45 |
| 2014/0276797 A1* | 9/2014 | Batchelor | A61B 18/1233 606/42 |
| 2014/0336629 A1* | 11/2014 | Scheib | A61B 17/320016 606/33 |
| 2015/0327913 A1 | 11/2015 | Horner | |
| 2016/0074098 A1* | 3/2016 | Kappus | A61B 18/1445 606/41 |
| 2017/0135712 A1 | 5/2017 | Boudreaux | |
| 2017/0303995 A1* | 10/2017 | Garrison | A61B 18/1445 |
| 2018/0271553 A1 | 9/2018 | Worrell | |
| 2020/0170701 A1* | 6/2020 | O'Keefe | A61B 17/00234 |

OTHER PUBLICATIONS

International Search Report and Written Opinion received for PCT/IB2020/052712, dated Sep. 3, 2020, 17 pages.

* cited by examiner

MONOPOLAR AND BIPOLAR FUNCTIONALITY

FIELD

Surgical devices, systems, and methods are provided for selectively applying monopolar energy and bipolar energy to tissue.

BACKGROUND

Various surgical devices can be used for minimally-invasive surgery to compress, transect, and seal different types of tissue. In general, these devices can have an end effector with a pair of opposed jaws that are configured to engage tissue therebetween and a cutting mechanism that is configured to transect tissue engaged by the opposed jaws. The end effectors can also be configured to apply electrical energy to tissue engaged between the opposed jaws. The application of electrical energy to the engaged tissue can seal and coagulate the tissue, such as to seal tissue being cut by the cutting mechanism to prevent or reduce bleeding.

However, various situations can arise during an operation in which a user wants to apply energy to tissue without having to first grasp tissue between the opposed jaws, such as being able to selectively apply energy to spots of tissue in a controlled manner without having to clamp and seal an entire section of tissue using bipolar energy.

Accordingly, there remains a need for improved energy delivery methods and devices for treating tissue.

SUMMARY

Methods, devices, and systems are provided herein for selectively applying monopolar energy to tissue adjacent to a surgical instrument and bipolar energy to tissue grasped by the surgical instrument during minimally-invasive surgery.

In one aspect, a surgical device is provided that includes a housing and an elongate shaft that extends from the housing and defines a longitudinal axis. An end effector is operatively connected to a distal end of the elongate shaft, and the end effector has first and second jaws. At least one of the jaws is movable between an open position in which the first and second jaws are spaced apart from one another and a closed position in which the first and second jaws cooperate to grasp tissue therebetween, and the first and second jaws are configured to conduct energy through tissue grasped therebetween. A conductive member extends longitudinally through the first jaw, and it has a hook on a distal end thereof. The conductive member has a proximal position in which the hook is disposed substantially within the first jaw and is oriented toward the second jaw and a distal position in which the hook is positioned distally to a distal end of the first jaw and is oriented away from the second jaw. Longitudinal translation of the conductive member is configured to cause the hook to move between the proximal position and the distal position.

The surgical device can have numerous variations. For example, longitudinal translation of the conductive member can be configured to automatically rotate the hook from being oriented toward the second jaw to being oriented away from the second jaw. In another example, at least part of the conductive member can be exposed to tissue adjacent to the first jaw in the proximal position such that energy can be applied to the tissue from the conductive member in the proximal position. The first jaw can also include a helical cam slot formed therein, and the conductive member can include a pin formed thereon that is disposed within the cam slot such that distal longitudinal translation of the conductive member can cause translation and rotation of the hook between the proximal position oriented toward the second jaw and the distal position oriented away from the second jaw. In still another example, energy can be supplied to the conductive member only in the distal position. In another example, energy can also be supplied to the first and second jaws only when the conductive member is in the proximal position. In one example, the first and second jaws can be configured to transect tissue grasped therebetween. In another example, the surgical device can include an electrically insulating sleeve that extends along a proximal portion of the conductive member and terminates proximal to the distal end thereof.

In another aspect, a surgical device is provided that includes a housing and an elongate shaft that extends from the housing and defines a first longitudinal axis. An end effector extends distally from the elongate shaft, and the end effector has first and second jaws. At least one of the jaws is movable between a spaced position for receiving tissue and a clamped position for engaging tissue. The first and second jaws are also configured to conduct energy through tissue grasped therebetween. A conductive rod extends through the elongate shaft and through the first jaw, and the conductive rod is axially translatable along the longitudinal axis. The conductive rod is axially translatable between a proximal position in which the conductive rod contacts an electrode on the first jaw to form a closed bipolar energy circuit that allows the first and second jaws to conduct energy through tissue grasped therebetween, and a distal position in which the conductive rod is electrically isolated from the electrode on the first jaw. The conductive member extends distally from the end effector to allow energy to be conducted through the conductive rod to tissue adjacent thereto.

The surgical device can have any number of different variations. For example, the surgical device can also include a articulation joint on a distal end of the elongate shaft that is configured to articulate the end effector relative to the first longitudinal axis of the elongate shaft. The conductive rod can also extend through the articulation joint and be configured to flex with the articulation joint during articulation of the joint. In another example, the conductive rod can be axially translatable when the articulation joint is articulated such that the first longitudinal axis of the elongate shaft intersects a second longitudinal axis of the end effector at a non-zero angle. In still another example, at least part of the conductive rod can also be exposed to tissue adjacent to the first jaw in the proximal position such that energy can be applied to the tissue from the conductive rod in the proximal position. The conductive rod can also have a conductive spring thereon that can be slidably engageable with the electrode on the first jaw. In one example, the conductive rod can have a hook formed on a distal-most end thereof, and the first jaw can be configured to receive the hook in a distal end thereof. In another example, the hook of the conductive rod can engage with the electrode on the first jaw in the proximal position to form a tissue contacting surface of the first jaw. In still another example, the first and second jaws can be configured to transect tissue grasped therebetween. In some examples, the conductive rod includes a cutting element.

In another aspect, a surgical method is provided that includes distally translating a conductive member through a first jaw of an end effector disposed on a distal end of a surgical device. Distal translation causes a hook disposed on a distal end of the conductive member to move from a retracted position in which the hook is disposed substantially within the first jaw and is oriented toward a second jaw of the end effector to an extended position in which the hook is positioned distally to a distal end of the first jaw and is oriented away from the second jaw. The method also includes actuating an energy assembly to supply energy to the conductive member to treat tissue located adjacent to the hook.

The surgical method can have numerous variations. In one example, the method can also include, after actuating the energy assembly, proximally translating the conductive member through the first jaw to cause the hook to move from the extended position to the retracted position. In another example, the surgical method can include actuating a trigger assembly on the surgical device to cause at least one of the first and second jaws to move to a closed position and grasp tissue therebetween. The method can also include actuating an energy assembly on the surgical device to supply energy to the first and second jaws to seal tissue grasped therein. In still another example, the surgical method can include actuating a cutting assembly on the surgical device to transect tissue grasped between the first and second jaws.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
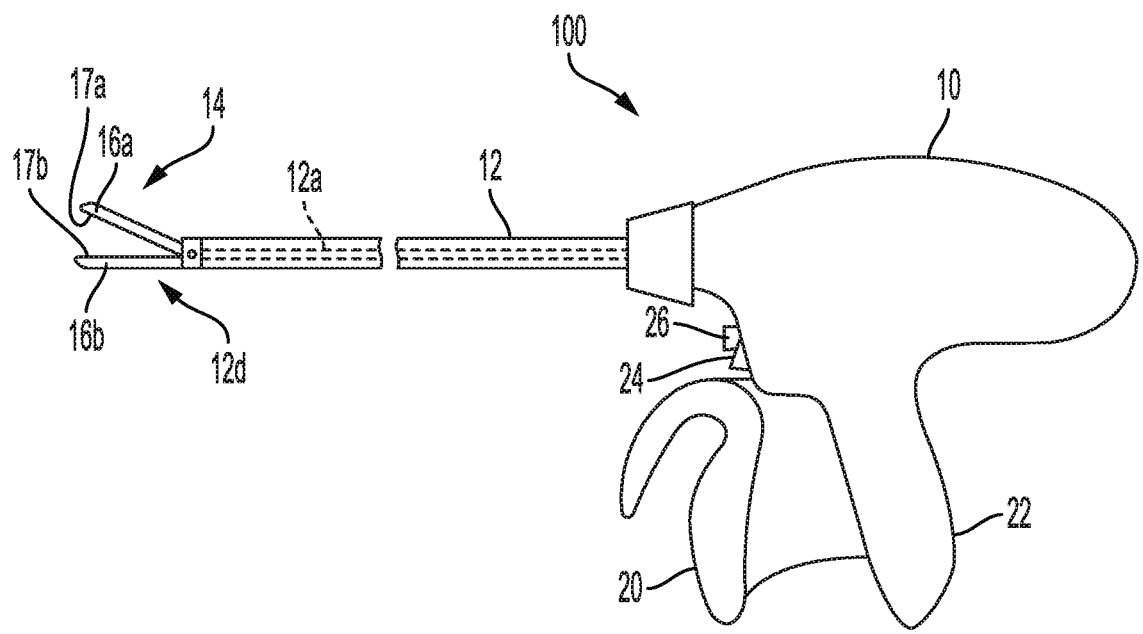
FIG. 1 is a side view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, devices, and systems are provided for applying energy to tissue in a monopolar treatment mode and a bipolar treatment mode using a surgical instrument, such as a minimally-invasive surgical instrument with an end effector that has opposed jaws for grasping tissue. The energy can be delivered to transect and/or seal tissue. While tissue sealing can be accomplished by applying energy between the opposed jaws to grasped tissue, it can also be beneficial to apply energy to target tissue that is adjacent to the end effector and not grasped thereby, such as by a "spot treatment." This can allow a user to conduct spot coagulation, non-clamping sealing and/or hemostasis, marking tissue, cutting or searing tissue, etc., during use. The energy applied to tissue grasped between the opposed jaws can be applied in a bipolar mode where the energy is applied by an energy delivering electrode in one jaw and received by a return electrode in the opposed jaw. In other aspects, spot energy can be applied to tissue adjacent to the end effector or a portion thereof in a monopolar mode. As such, various monopolar electrodes are provided that can be advanced from end effectors of surgical instrument for applying spot energy to target tissue, and retracted into the end effectors for storage therein when energy delivery is not necessary. When advanced, at least part of the monopolar electrode can protrude distally from the end effector to deliver energy to tissue adjacent thereto, and when retracted, the monopolar electrode can be at least partially withdrawn proximally into the end effector for storage such that at least a portion of the electrode is protected by the end effector.

In an exemplary embodiment, a surgical device is provided that has a housing with an elongate shaft extending distally therefrom. An end effector having first and second jaw is operatively connected to a distal end of the elongate shaft. At least one of the first and second jaws is movable between an open position in which the first and second jaws are spaced apart from one another and a closed position in which the first and second jaws cooperate to grasp tissue therebetween. In the closed position, the first and second jaws can conduct energy through tissue grasped therebetween. A conductive member extends longitudinally through the first jaw, and it can have a retracted or proximal position and an extended or distal position. In the retracted position, the conductive member is substantially disposed within the first jaw, and in the extended position, a distal end of the conductive member is positioned distally to a distal end of the first jaw. The conductive member can be configured to conduct energy to tissue adjacent thereto. The conductive member can take a variety of forms and can translate longitudinally in a variety of ways, as discussed in detail below.

FIG. 1 illustrates one embodiment of a surgical device configured to grasp and cut tissue. As shown, the illustrated surgical device 100 generally includes a proximal housing portion 10, a shaft portion 12, and an end effector 14 for grasping tissue. The proximal housing portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal housing portion 10 includes a stationary grip 22 and a closure grip 20 that is movable relative to the stationary grip 22 to open and close jaws of the end effector 14. The shaft portion 12 extends distally from the proximal housing portion and has at least one lumen 12a extending therethrough for carrying mechanisms for actuating the end effector 14. The end effector 14 can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, as shown in FIG. 1, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can act to engage or grasp tissue therebetween. In the illustrated embodiment, the upper jaw 16a pivots relative to the shaft portion 12 and relative to the lower jaw 16b while the lower jaw 16b remains stationary, however in other embodiments both jaws can pivot, or the lower jaw 16b can pivot while the upper jaw 16a remains stationary.

While the illustrated jaws 16a, 16b have a substantially elongate and straight shape, a person skilled in the art will appreciate that one or both of the jaws 16a, 16b can curve in various directions, such as being curved along a longitudinal length thereof. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14 such that the jaws can engage tissue, move anatomical structures, or perform other surgical functions. While the closure actuator can have various configurations, in the illustrated embodiment the closure actuator includes the closure grip 20 and the stationary grip 22. The closure grip 20 can be pivotal toward and away from the stationary grip 22. In particular, the closure grip 20 can have a first or initial open position in which it is angularly offset and spaced apart from the stationary grip 22 and the jaws 16a, 16b of the end effector 14 are open. It can also have a second or final closed position where it is positioned adjacent to, or substantially in contact with, the stationary grip 22 and the jaws 16a, 16b of the end effector 14 are substantially closed to engage tissue and apply a force to tissue disposed therebetween. The closure grip 20 can be biased to the first open position with the jaws 16a, 16b of the end effector 14 being open, as shown in FIG. 1.

The closure grip 20 can use manual or powered components. In manual embodiments the closure handle 20 is configured to be manually moved (e.g., by a user directly or by a user indirectly via robotic surgical control) to manually open/close the end effector 14 using various components, e.g., gear(s), rack(s), drive screw(s), drive nut(s), etc. disposed within the housing 10 and/or shaft 12.

Figure 3:
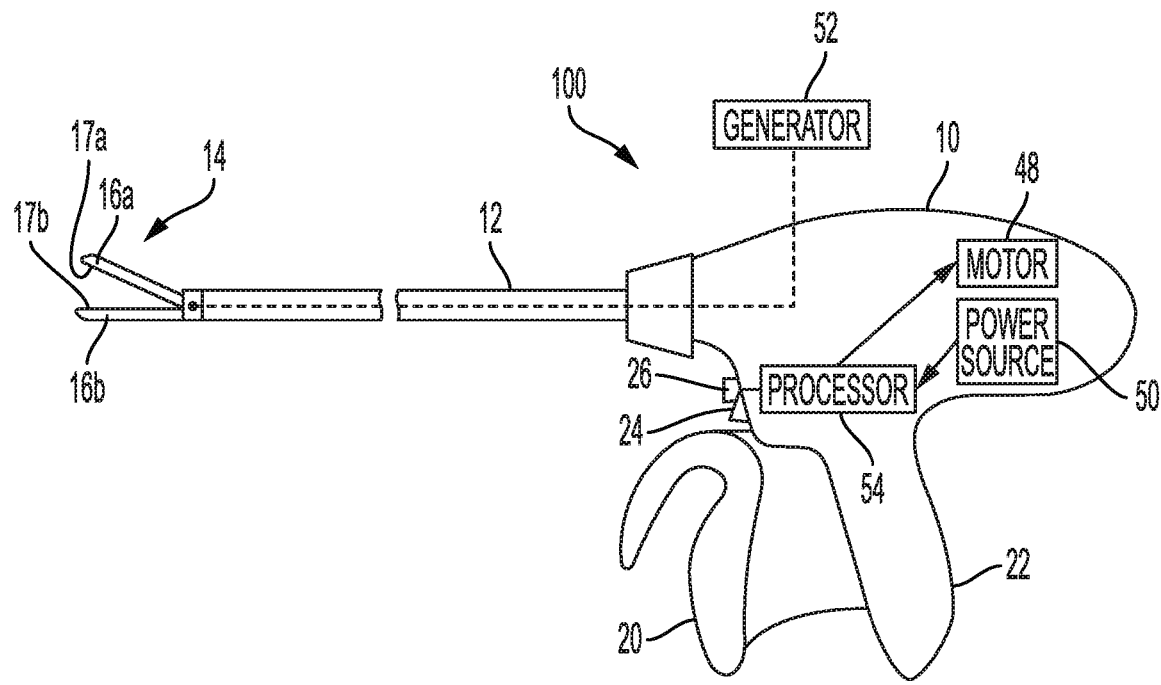
FIG. 3 is another side view of the surgical device of FIG. 1.

In powered embodiments, the closure handle 20 is configured to be manually moved (e.g., by a user directly or by a user indirectly via robotic surgical control), thereby causing the end effector 14 to open/close either fully electronically or electronically in addition to manual power. In this illustrated embodiment, as shown in FIG. 3, the device 100 is powered and includes a motor 48, a power source 52, and a processor 54, which in this illustrated embodiment are each disposed in the housing 10. Manual movement of the closure handle 20 is configured to cause the processor 54 to transmit a control signal to be sent to the motor 48, which is configured to interact with various components of the device 100 to cause the jaws 16a, 16b to open/close. The power source 52 is configured to provide on-board power to the processor 54 and the motor 48. In other embodiments, the processor 54 and/or the motor 48 can be configured to be powered instead, or additionally, with an external power source. The device 100 can include one or more sensors to facilitate powered end effector opening and closing and/or other device features, such as tissue cutting. Various embodiments of such sensors are further described in U.S. Pat. No. 7,416,101 entitled "Motor-Driven Surgical Cutting And Fastening Instrument With Loading Force Feedback" filed Jan. 31, 2006 and U.S. Pat. No. 9,675,405 entitled "Methods And Devices For Controlling Motorized Surgical Devices" filed Apr. 8, 2014, which are hereby incorporated by reference in their entireties. Further description of embodiments of end effector opening and closing is provided in U.S. Pat. No. 10,010,309 entitled "Surgical Device With Overload Mechanism" filed Oct. 10, 2014, which is hereby incorporated by reference in its entirety.

In at least some embodiments the closure grip 20 can also interact with one or more locking features to lock the closure grip 20 relative to the stationary handle 22, as will be appreciated by a person skilled in the art. For example, the locking feature can automatically engage when the closure grip 20 substantially contacts the stationary handle 22 or the locking feature can automatically engage at each position the closure grip 20 is pivoted through, such as via ratcheting.

Figure 2:
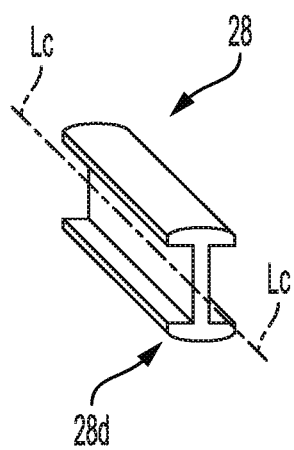
FIG. 2 is a perspective view of a compression member of the surgical device of FIG. 1.

The surgical device 100 can also have one or more additional activators that can be separate from the closure actuator 20, such as a cutting actuator 24 to advance a cutting assembly and one or more sealing actuators 26 to apply energy to tissue. While the actuators 24, 26 can have various configurations, the illustrated actuators 24, 26 are buttons or triggers that can be depressed by a user and can activate various elements in the device to advance the cutting element and/or cause energy to be delivered to the jaws. For example, the cutting actuator 24 can be in manual or electrical communication with various gear(s), rack(s), drive screw(s), drive nut(s), motor(s), and/or processor(s). The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels along a longitudinal axis Lc through slots formed in each jaw to pull the jaws into a parallel orientation, to compress tissue therebetween, and to transect tissue using a cutting element on the distal end 28d thereof. As shown in FIG. 3, the housing portion 10 of the surgical device 100 can include other components for operating the device, such as the motor 48, a power source 50, a generator 52, and/or the processor 54, as well as various sensors (not shown).

The surgical device 100 includes a sealing actuator 26 configured to be actuated to cause energy, such as radiofrequency (RF) or ultrasound energy, to be applied to tissue engaged by the end effector 14. While the actuator 26 can have various configurations, e.g., buttons, knobs, triggers, etc., the illustrated actuator 26 is a button configured to be depressed. In other embodiments, instead of including a cutting actuator 24 and a sealing actuator 26, a surgical device can include a combined cutting and sealing actuator configured to be actuated to simultaneously cause cutting and sealing.

The device 100 includes various components configured to facilitate the delivering of energy to tissue. These components can be disposed at various locations in the device 100, such as in the proximal housing portion 10 and/or in one or both of the jaws 16a, 16b. Actuating the sealing actuator 26 is configured to cause a signal to be transmitted to the processor 54, which in response is configured to cause delivery of energy from the generator 52 and/or the power source 50 to tissue engaged by the end effector 14. The generator 52 can be incorporated into the housing portion 10 or, as in this illustrated embodiment as shown in FIG. 3, can be a separate unit that is electrically connected to the surgical device 100. The generator 52 is any suitable generator known in the art, such as an RF generator or an ultrasound generator.

The lumen 12a of the shaft 12 has disposed therein one or more electrical paths 46, e.g., leads, conductive members, wires, etc., configured to deliver electrical energy to the end effector 14 in response to actuation of the sealing actuator 26. The one or more electrical paths 46 are operatively coupled to the generator 52 in this illustrated embodiment, with the generator 52 being configured to supply energy to the one or more electrical paths 46. Upon actuation of energy delivery, energy is configured to be delivered to one or more electrodes in one or both of the jaws 16a, 16b via the one or more electrical paths 46 for delivering electrical current to tissue grasped therebetween to effect sealing, marking, cutting, etc. of the tissue. Further description of embodiments of energy application by surgical devices is provided in U.S. Pat. No. 10,010,366 entitled "Surgical Devices And Methods For Tissue Cutting And Sealing" filed Dec. 17, 2014, U.S. Pat. No. 7,169,145 entitled "Tuned Return Electrode With Matching Inductor" filed Nov. 21, 2003, U.S. Pat. No. 7,112,201 entitled "Electrosurgical Instrument And Method Of Use" filed Jan. 22, 2003, and U.S. Patent Pub. No. 2017/0135712 entitled "Methods And Devices For Auto Return Of Articulated End Effectors" filed Nov. 17, 2015, which are hereby incorporated by reference in their entireties.

The device 100 has bipolar functionality in which energy applied to tissue engaged by the end effector 14 is energy applied by a delivery or active electrode 17a and received by a return electrode 17b. One of the jaws 16a, 16b (the upper jaw 16a in this illustrated embodiment) includes the active electrode 17a on a tissue-facing surface thereof, and the other one of the jaws 16a, 16b (the lower jaw 16b in this illustrated embodiment) includes the return electrode 17b on a tissue-facing surface thereof. The return electrode 17b is electrically isolated from the active electrode 17a such that energy can be applied to tissue grasped between the jaws 16a, 16b from the active electrode 17a and have a return path through the return electrode 17b. The energy is thus configured to be delivered to tissue grasped between the jaw 16a, 16b when the end effector 14 is in the closed position.

While energy can be delivered to tissue grasped between the opposed jaws 16a, 16b in the device 100 in a bipolar mode, energy can also be delivered to tissue without having to grasp tissue by advancing one or more monopolar electrodes from the end effector. FIGS. 4A-4H illustrate an embodiment of a surgical device 200 similar to surgical device 100. All of the aforementioned features of device 100 are present on device 200. In particular, surgical device 200 has an end effector 214, an elongate shaft 212, and a housing, which can be in the form of a handle (not shown). The shaft 212 extends distally from the housing and has the end effector 214 disposed on a distal end thereof, and it has at least one lumen 212a extending therethrough for carrying mechanisms for actuating the end effector 214. The end effector 214 has a first upper jaw 216a and a second lower jaw 216b that is opposed thereto. The jaws 216a, 216b can grasp tissue therebetween, transect grasped tissue with a cutting element 218, and apply energy in a bipolar mode to grasped tissue through active and return electrodes 219a, 219b in the jaws 216a, 216b. The handle includes a stationary grip and a closure grip (not shown) that is pivotally movable relative to the stationary grip to open and close upper and lower jaws 216a, 216b of the end effector 214. A cutting actuator (not shown) is disposed on the housing to cause transection by the cutting element 218 of tissue grasped by the jaws 216a, 216b, and an energy actuator (not shown) is disposed on the housing to cause delivery of energy to the end effector 214. Various gear(s), rack(s), drive screw(s), drive nut(s), motor(s), processor(s), conducting member(s), etc. can be disposed within the handle and/or the shaft 212 to translate actuation of the closure grip and various actuator(s) into actuation of functions on the end effector 214.

Figure 4A:
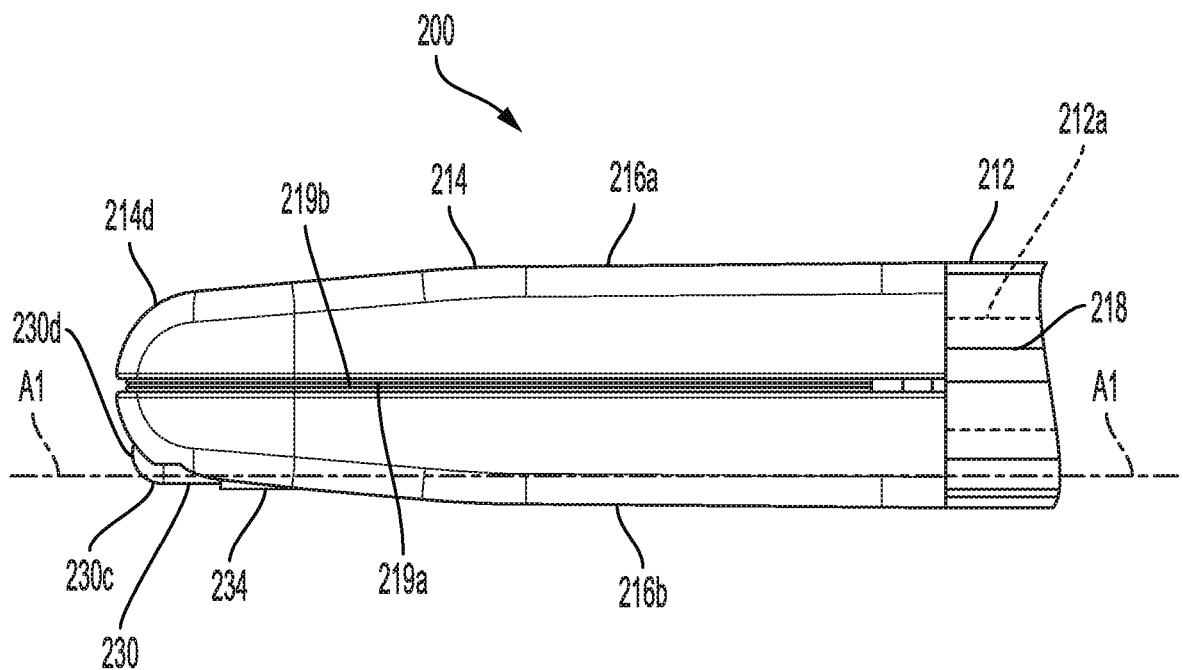
FIG. 4A is a side view of an end effector and a shaft of another embodiment of a surgical device.
Figure 4B:
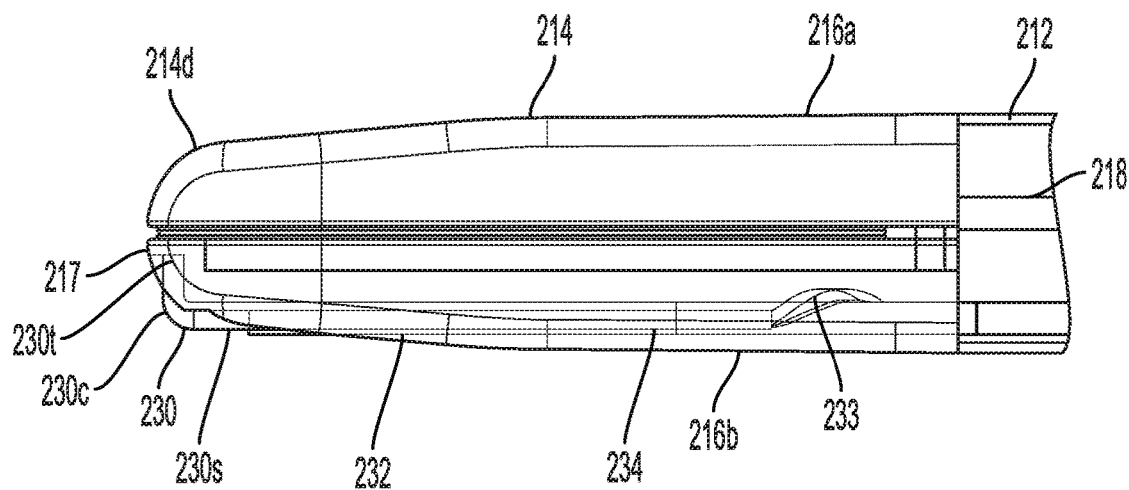
FIG. 4B is a partially-transparent side view of the end effector of FIG. 4A.
Figure 4C:
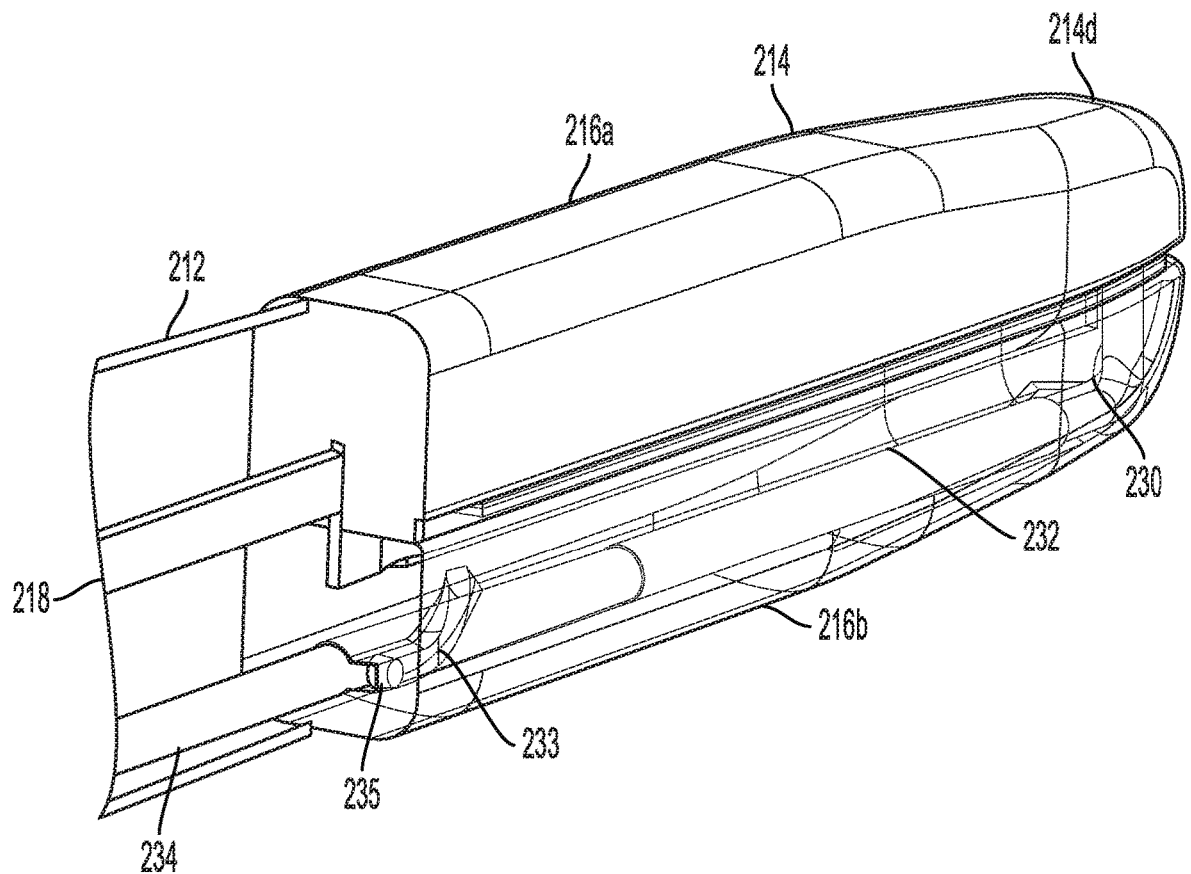
FIG. 4C is a partially-transparent perspective view of the end effector of FIG. 4A.
Figure 4D:
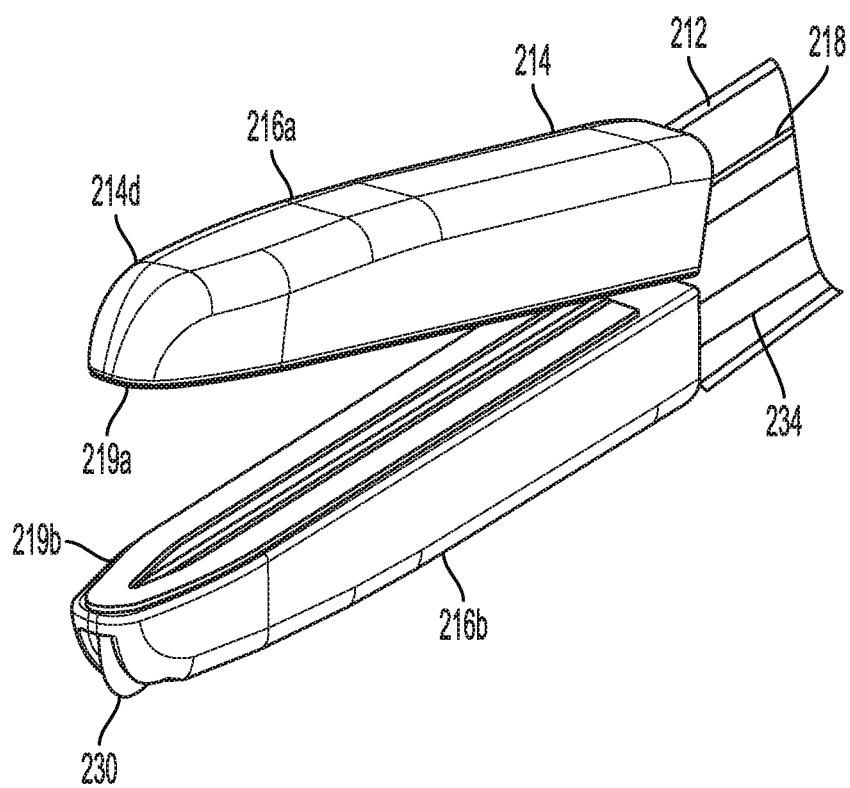
FIG. 4D is a perspective view of the end effector of FIG. 4A with open jaws.

A monopolar electrode 230 extends longitudinally through at least a portion of the end effector 214 and is longitudinally translatable distally and proximally with respect thereto. The electrode 230 can translate between a retracted position in which a majority of the electrode 230 is retracted within the end effector 214, as illustrated in FIGS. 4A-4D, and an extended position in which at least a distal end 230d of the electrode 230 protrudes distally beyond a distal end 214d of the end effector 214, as illustrated in FIGS. 4F-4H. Upon distal translation of the electrode 230 and actuation of energy, as discussed below, the electrode 230 can be used to spot seal, coagulate, mark, cut, etc. tissue disposed adjacent to the distal end 214d of the end effector 214. While the illustrated electrode 230 extends through the end effector and the shaft 212, it can extend parallel to but outside of one or both of the end effector 214 and the shaft 212 in other embodiments.

While the configuration can vary, in the illustrated embodiment the electrode 230 has a general shape of an L with an elongate rod 230s and a hook or bent tip 230t on a distal end thereof that extends at an approximately right angle thereto. The rod 230s extends proximally through a longitudinal electrode lumen 232 that extends through the lower jaw 216b to engage with one or more conductive members, such as wires or other electrical leads, in the handle of the surgical device 200 for receiving energy therefrom.

The electrode 230 also has a non-conductive protective sleeve 234 that insulates a majority of the electrode rod 230s as it extends through the device 200 while terminating proximal to the hook 230t. As such, the electrode 230 has an exposed, electrically-active distal portion. The sleeve 234 can thus help protect various components within the device 200 and any secondary tissue from inadvertent electrical exposure while creating an easily-identifiable active distal end on the electrode 230 for treatment of any target tissue. In some embodiments, the end effector 214, the shaft 212, and/or the handle thus do not need to be electrically insulated, however one or more portions thereof can be insulated as desired to prevent energizing unintended areas. The sleeve 234 can be made from a variety of insulating materials, such as PVC wire insulation.

In the retracted position, the hook 230t can be received in a distal tip notch 217 on a distal end of the lower jaw 216b, and it can extend toward the upper jaw 216a. As illustrated in FIGS. 4A and 4B, at least a portion of the electrode 230, such as a corner 230c, can still protrude from the lumen 232 and the notch 217 such that surrounding tissue can still be exposed to and spot treated by the electrode 230 even in the retracted position. As such, a user can perform minor tissue modifications, such as limited spot coagulation, without having to extend the electrode. However, a majority of the electrode 230 is received into the end effector 214 in the retracted position, and energy delivery from the electrode 230 can be selectively terminated so that no energy is delivered therefrom. This can avoid any accidental energy application during movement, treatment, etc. Furthermore, in other embodiments, the electrode can be withdrawn entirely into the end effector. While the notch 217 extends toward the upper jaw 216a, in other embodiments the notch can be oriented in a variety of different ways, such as parallel to a plane that passes through a tissue contacting surface of the upper jaw 216a.

Figure 4E:
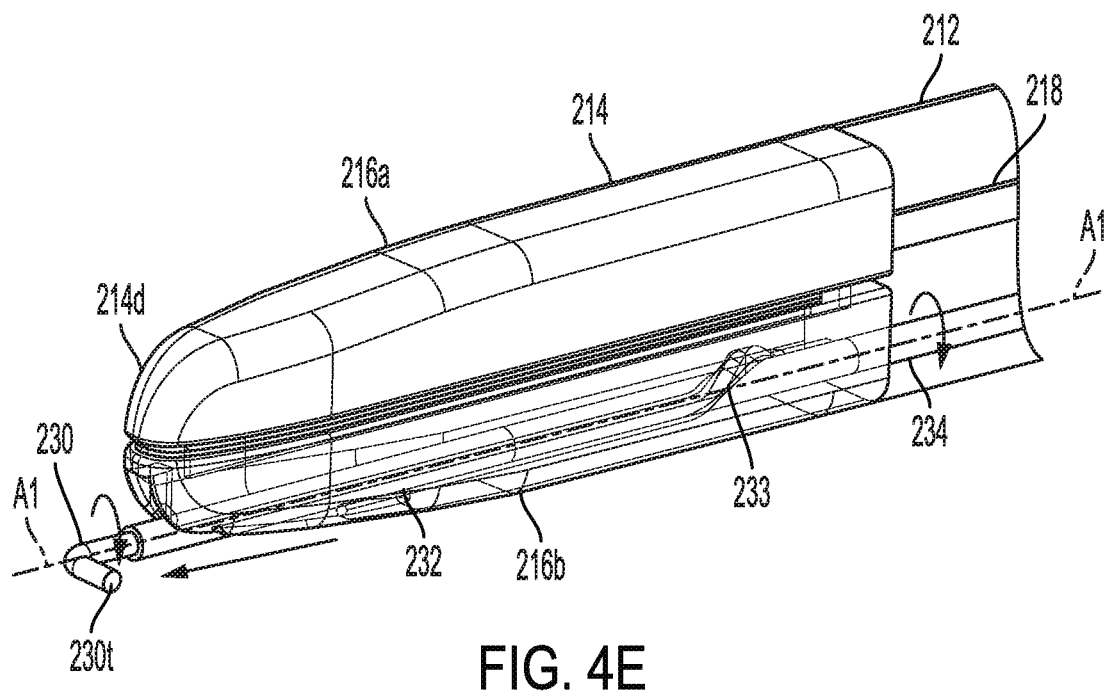
FIG. 4E is a partially-transparent perspective view of the end effector of FIG. 4A with a conductive member in the process of translating distally and rotating.
Figure 4F:
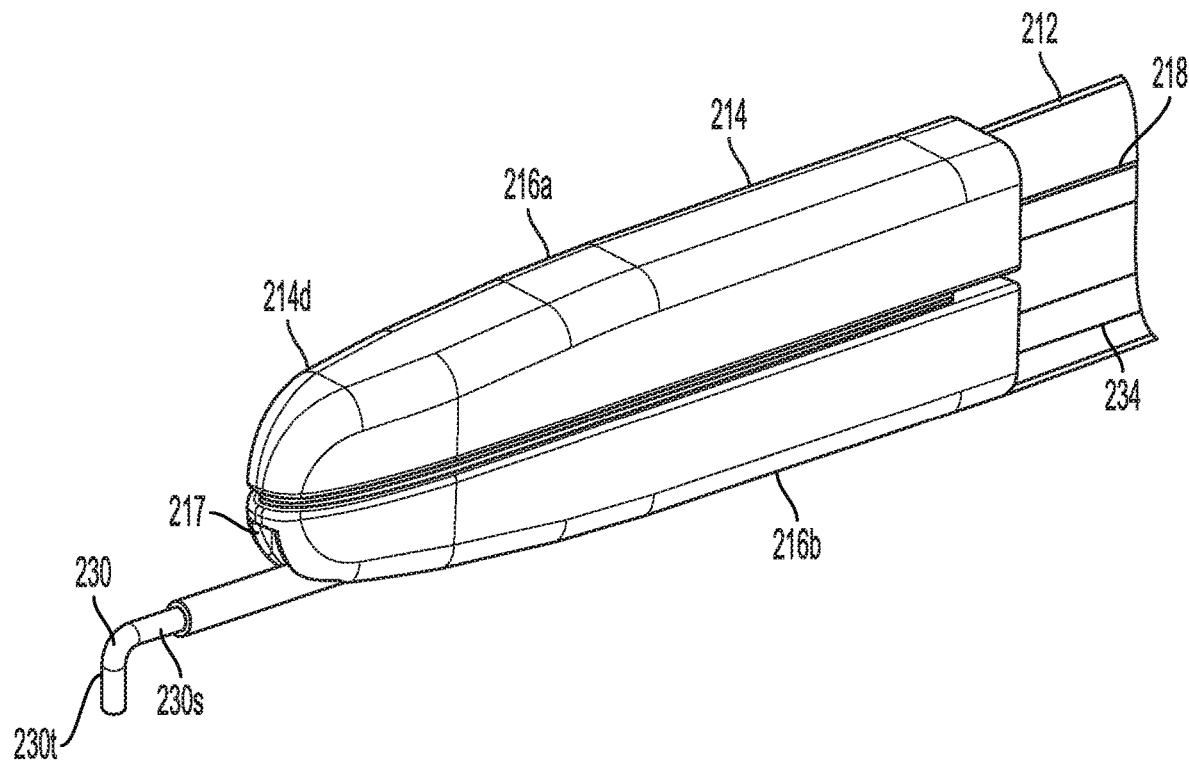
FIG. 4F is a perspective view of the end effector of FIG. 4A with the conductive member extended distally.
Figure 4G:
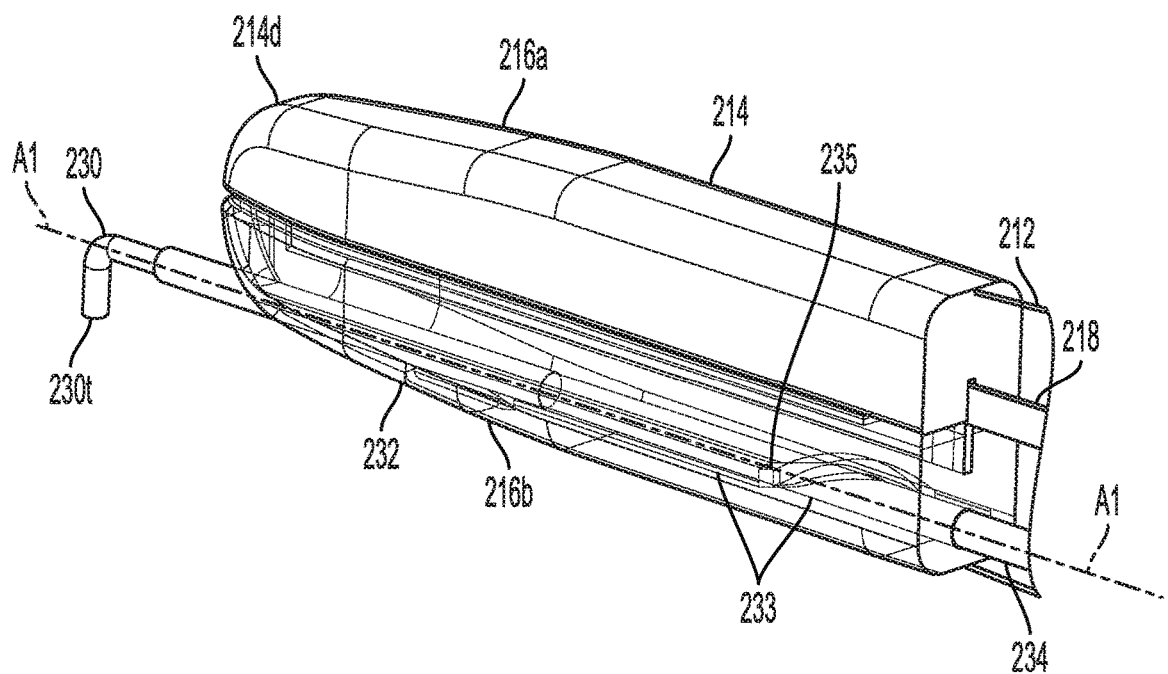
FIG. 4G is a partially-transparent perspective view of the end effector of FIG. 4A with the conductive member extended distally.
Figure 4H:
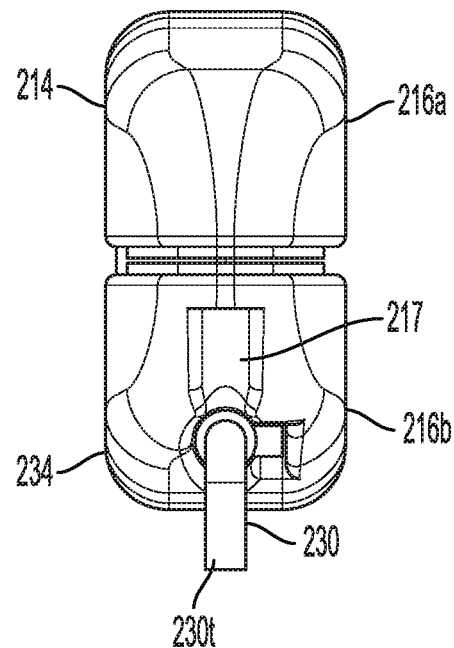
FIG. 4H is a front view of the end effector of FIG. 4A with the conductive member extended distally.

During extension of the electrode 230, the rod 230s and the hook 230t can be rotatable about a longitudinal axis A1 of the shaft, as illustrated in FIG. 4E. The hook 230t has a set rotational movement during distal extension such that it protrudes away from the upper jaw 216a upon full distal extension, as illustrated during partial rotation and extension in FIG. 4E and full rotation and extension in FIGS. 4F-4H, to provide increased visibility and energy treatment accessibility when in the extended position. The set rotational movement is caused by a pin 235 protruding from the rod 230s of the electrode 230 and/or the sleeve 234 and resting in a rotational guide slot 233 that is in communication with the electrode lumen 232 through the lower jaw 216b, as illustrated in FIGS. 4C and 4G. The rotational guide slot 233 receives the pin 235 therein, and during distal translation along axis A1, the pin 235 initially translates longitudinally along the rotational guide slot 233. The slot 233 initially extends parallel to the lumen 232 on a first side of the lower jaw 216b. However, after initially extending parallel to the lumen 232, the guide slot 233 begins to curve in a semicircular helical or corkscrew path around the electrode lumen 232. The helical path is arranged such that, when the hook 230t of the electrode reaches a distal extension at which it is rotationally clear of the distal tip notch 217 in the lower jaw 216a, the pin 235 begins to curve around the helical path of the guide slot 233. This causes rotation of the hook 230t from its initial position protruding toward the upper jaw 216a to its fully-extended position protruding away from the upper jaw 216a, as illustrated by arrows indicating rotation and distal translation in FIG. 4E. The hook 230t thus rotates approximately 180 degrees. Upon complete rotation of the electrode 230, shown in FIGS. 4F-4H, the pin 235 comes to rest in the guide slot 233 on a second side of the lower jaw 216b opposite to the first side. In the illustrated embodiment, the guide slot 233 continues to extend distally parallel to the electrode lumen 232 on the second side of the lower jaw 216b to the distal end of the lower jaw 216b to allow continued distal extension of the electrode 230 if desired. However, in other embodiments, the pin 235 can come to rest at a terminal distal end of the guide slot 233 proximal to the distal end of the lower jaw 216b to assist in maintaining a controlled distal protrusion distance of the electrode 230. Upon retraction of the electrode 230, proximal translation of the electrode 230 causes a corresponding proximal helical motion of the pin 235 in the guide slot 233 such that the hook 230t translates and rotates proximally to the stored, retracted position in the lower jaw 216b. The pin 235 and the guide slot 233 thus act as a type of camming mechanism to cause automatic rotation of the hook 230t during distal translation.

As such, energy can be delivered to tissue without having to first grasp tissue by energizing the exposed corner portion 230c when the electrode 230 is retracted in the end effector 214, or by extending the hook 230t distally to the extended position while rotating the hook 230t through an approximately 180 degree automatic helical rotation to help improve visibility and exposure of the energized hook 230t to tissue adjacent thereto to touch, drag along, mark, cut, coagulate, etc. the tissue. In still other embodiments, the electrode 430 can be selectively rotatable by a user through a rotational mechanism on the handle, such as by using a rotational knob, dial, etc. The hook 230t can thus protrude radially outward in any of 360 degrees of rotation relative to the rod 230s in some embodiments. The electrode 230 can be made from a variety of electrically-conductive materials, such as metal.

Distal and proximal translation of the electrode 230 can be controlled by a variety of different mechanisms. In the illustrated embodiment, pivotal movement of the closure grip relative to the stationary grip through a select range of motion causes distal and proximal translation, similar to the mechanism discussed in U.S. patent application Ser. No. 16/375,534, entitled "Monopolar And Bipolar Functionality," filed concurrently herewith, which is incorporated by reference herein in its entirety. However, a variety of other mechanisms can be used, such as by having a separate pivotal grip or lever on the handle, by having a sliding mechanism on the handle, by having a rotational knob positioned between the handle and the shaft 212 that can cause axial rotation of the shaft 212 by rotation of the knob and/or longitudinal translation of the electrode 230 by distal and proximal translation of the knob relative to the handle, by one or more buttons or switches on the handle that can cause powered translation through one or more gear mechanisms therein, etc.

Energy can be applied to the electrode 230 through various mechanisms, as well. In the illustrated embodiment, energy can is applied to the monopolar electrode 230 similar to energy applied to electrodes 219a, 219b targeting grasped tissue in the end effector 214. An energy actuator on the handle of the device 200 can be depressed, actuating delivery of energy through one or more conductive members from a generator, similar to generator 52, and/or a power source, similar to power source 50, to the electrode 230. In some embodiments, the device 200 can restrict energy from being transmitted to the electrode 230 until the electrode 230 is in the extended position, at which point depression of the actuator 226 can supply energy to electrode 230 and not electrodes 219a, 219b. For example, the device 200 can use a position sensor in the handle that detects a proximal position of the rod 230s, determining if it is in the retracted position (such that energy is restricted to the electrode 230) or in the extended position (such that energy is restricted to the electrodes 219a, 219b). In other embodiments, the device 200 can transition between monopolar and bipolar modes upon actuation of the pivotal grip, lever, rotational knob, etc. that causes the electrode 230 to extend distally. In still other examples, this determination can be made through use of various rotational, magnetic, switch, pressure, etc. sensors. A user can also activate a button or switch on the handle of the device 200 to transition between a monopolar and a bipolar mode. Furthermore, in some embodiments, energy delivery can be directed to the electrodes 219a, 219b and/or the electrode 230 through a position of the energy actuator. In particular, the energy actuator can have two ranges of motion, and it can apply energy to the electrodes 219a, 219b when moved through an initial first range, and it can apply energy to the electrode 230 when further depressed and moved through a second range. This can be preferable, for example, when limited spot treatment of tissue is desired when the electrode 230 is not in the extended position but instead has the small corner portion 230c exposed when it is in the retracted position. In other embodiments, actuation can occur through an entirely separate actuation mechanism than the actuation mechanism for the electrodes 219a, 219b, such as a separate button, switch, etc. on the handle. In still other embodiments, actuation mechanisms can be limited to one actuator that is used both for cutting and energy actuation. In various embodiments, energy actuation can allow selective application of more than one electrical waveform to the monopolar electrode 230, such as having one continuous low-voltage waveform for tissue cutting and another interrupted high-voltage waveform for tissue and blood coagulation. When energy is applied to the electrode 230 in the monopolar mode, energy applied to a target tissue can dissipate and return through a ground pad placed on a patient's body, etc.

The device 200 can be used in a manner similar to device 100 when grasping tissue between the jaws 216a, 216b, transecting the grasped tissue, and applying energy thereto. The electrode 230 can initially be in the retracted position, and the device 200 can operate in a bipolar mode. When spot application of energy is desired, the electrode 230 can be translated from the retracted position to the extended position, as discussed above. As the electrode 230 extends distally, the hook 230t can rotate through the helical path of the guide slot 233 such that the hook 230t rotates approximately 180 degrees from facing toward the upper jaw 216a to facing away from the upper jaw 216a as it extends distally. Once the electrode 230 is extended in the monopolar mode, energy can then be applied to target tissue by the exposed distal portion of the electrode 230. The electrode 230 can then be translated to the retracted position, again causing rotational movement of the hook 230t to be stored in the retracted position in the end effector 214, and a user can proceed with using the device 200 in the bipolar mode. In embodiments in which the electrode 230 can be actuated without first extending it, energy can be applied to the electrode 230 in the retracted position, and the user can spot treat limited portions of tissue as desired using the exposed corner portion 230c. In various embodiments, the electrode 230 can also be extended only when the jaws 216a, 216b are in the closed position, only when the jaws 216a, 216b are in the opened position, or either when the jaws 216a, 216b are opened or closed.

In other embodiments, rotation of the monopolar electrode is not required when moving the electrode between a retracted position and an extended position. Rather, extension of the electrode can occur primarily through linear axial translation. FIGS. 5A-5F illustrate a surgical device 300, similar to surgical devices 100, 200, that has an electrode 330 that is translated between retracted and extended positions. The device 300 has an end effector 314, an elongate shaft 312, and a housing such as a handle (not shown). The shaft 312 extends distally from the housing and has the end effector 314 disposed on a distal end thereof, and it has at least one lumen 312a extending therethrough for carrying mechanisms for actuating the end effector 314. The end effector 314 has a first upper jaw 316a and a second lower jaw 316b that is opposed thereto. The jaws 316a, 316b can grasp tissue therebetween, transect grasped tissue with a cutting element 318, and apply energy in a bipolar mode of operation to grasped tissue through active and return electrodes 319a, 319b in the jaws 316a, 316b. The housing includes a pivotal closure grip (not shown) that is pivoted to open and close upper and lower jaws 316a, 316b and one or more actuators (not shown) to cause transection of tissue grasped by the jaws 316a, 316b and delivery of energy to the end effector 314. Various gear(s), rack(s), drive screw(s), drive nut(s), motor(s), processor(s), conducting member(s), etc. can be disposed within the handle and/or the shaft 312 to translate actuation of the closure grip and various actuator(s) into actuation of functions on the end effector 314, as described above.

Figure 5A:
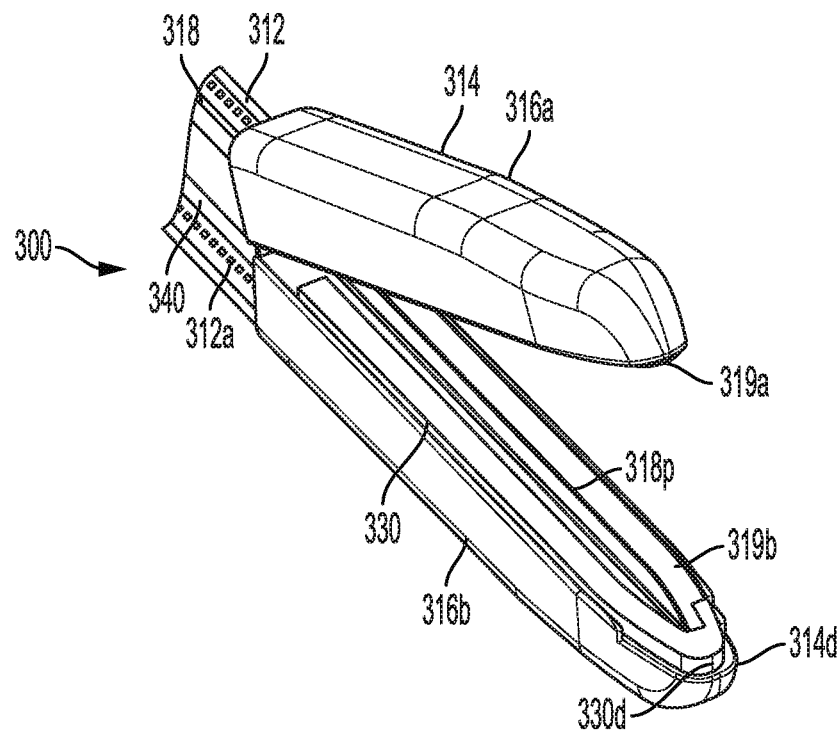
FIG. 5A is a perspective view of an end effector with open jaws and a shaft of another embodiment of a surgical device.
Figure 5B:
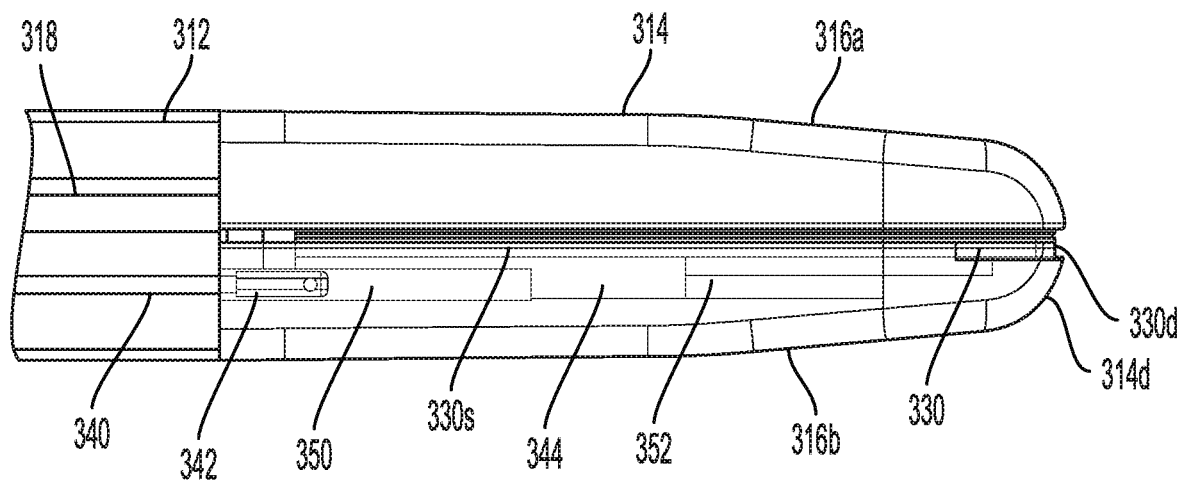
FIG. 5B is a partially-transparent side view of the end effector of FIG. 5A.
Figure 5C:
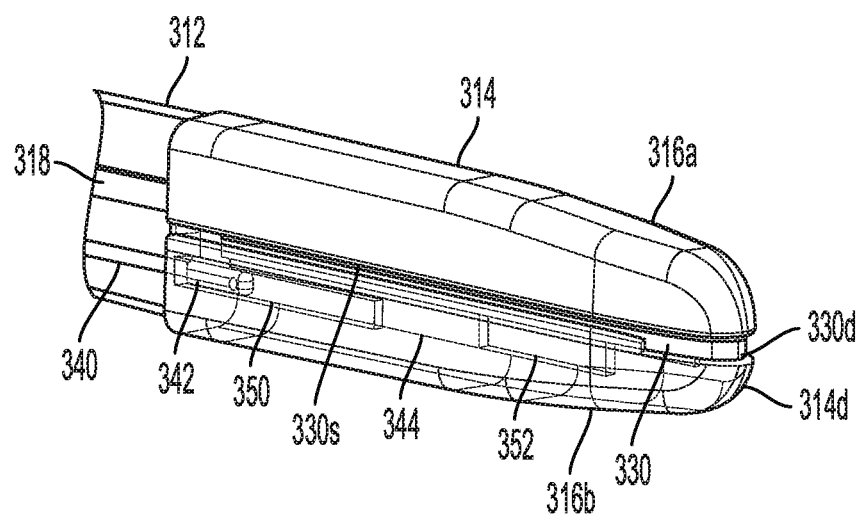
FIG. 5C is a partially-transparent perspective view of the end effector of FIG. 5A.
Figure 5D:
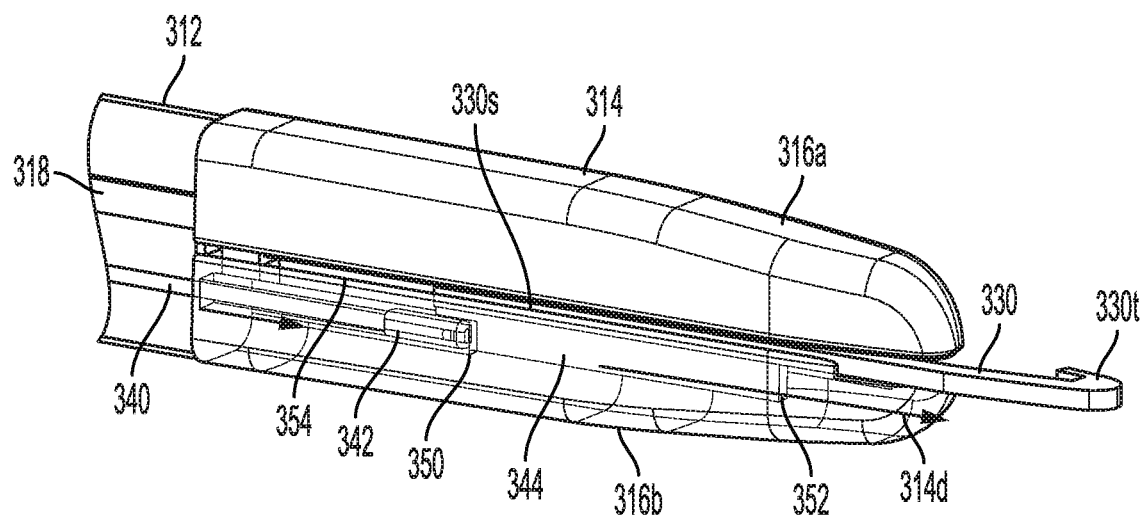
FIG. 5D is a partially-transparent perspective view of the end effector of FIG. 5A with a conductive member in the process of translating distally.
Figure 5E:
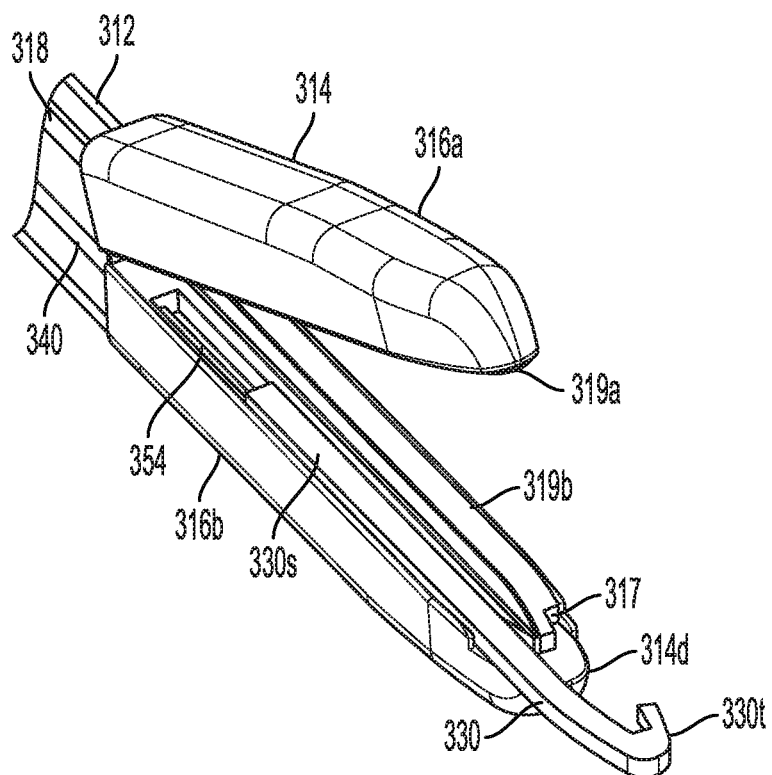
FIG. 5E is a perspective view of the end effector of FIG. 5A with open jaws and the conductive member extended distally.
Figure 5F:
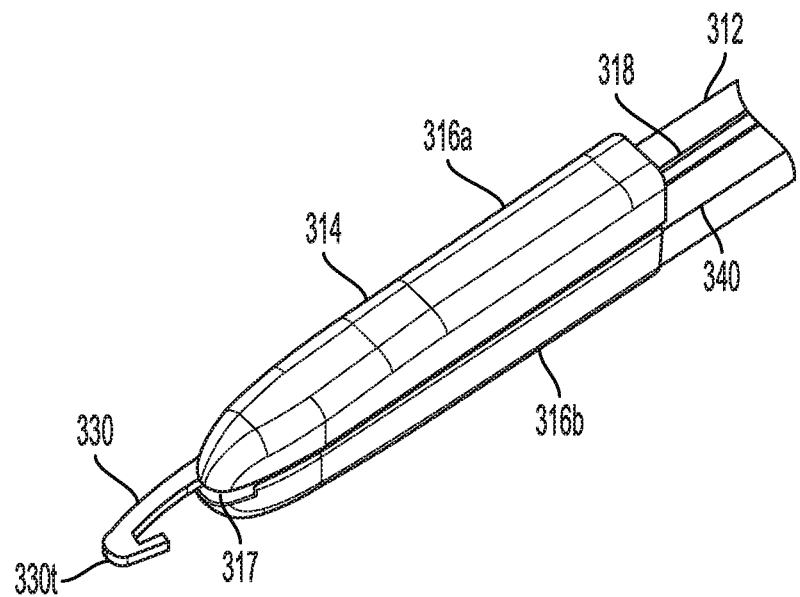
FIG. 5F is a perspective view of the end effector of FIG. 5A with the conductive member extended distally.

The electrode 330 extends longitudinally through the end effector 314 and is axially translatable distally and proximally, similar to electrode 230. The electrode 330 can translate between a retracted position in which a majority of the electrode 330 is retracted within the end effector 314, as illustrated in FIGS. 5A-5C, and an extended position in which at least a distal end 330d of the electrode 330 protrudes distally beyond a distal end 314d of the end effector 314, as illustrated in FIGS. 5D-5F. When the electrode 330 is in the retracted position, the electrode 330 forms part of the bipolar electrical pathway of the jaws 316a, 316b, as illustrated in FIG. 5A and discussed below. Upon distal translation of the electrode 330, the electrode 330 can act as a monopolar electrode, similar to electrode 230, as a result of electrically decoupling itself from the bipolar electrode 319b, as discussed below. Thus, similar to electrode 230, upon distal transition of the electrode 330 and actuation of energy, the electrode 330 can be used to spot seal, coagulate, mark, cut, etc. tissue disposed adjacent to the end effector 314.

The electrode 330 has a general J shape with a proximal flat extension 330s and a distal hook 330t. The flat extension 330s extends along a tissue contacting surface of the lower jaw 316b of the end effector 314 and is positioned on an opposite side of the jaw 316b from the bipolar electrode 319b such that a cutting element translation path 318p extends longitudinally between the flat extension 330s and the bipolar electrode 319b and along a center of the lower jaw 316b. The flat extension 330s is positioned in an electrode channel 354 that has an opening at the distal end of the lower jaw 316b to allow for distal and proximal translation of the electrode 330 to distally extend at least partially out of the channel 354 when the electrode 330 is in the monopolar mode. The distal hook 330t is a curved hook that generally corresponds to a curvature of the distal end of the lower jaw 316b (and thus the curvature of the distal end 314d of the end effector 314), and it curves such that a terminal end thereof protrudes proximally away from the distal end 314d of the end effector 314 when in the retracted position.

The electrode 330 can engage with one or more conductive members that extend proximally through the shaft 312 and into the handle to receive energy therefrom and are linearly translated thereby. A conductive rod 340 extends proximally at least partially through the shaft 312 to convey energy from an energy source, and it extends at least partially distally into a first guide slot 350 in the lower jaw 316b. The conductive rod 340 mates with a planar member 344 through a conductive engagement cap 342. The planar member 344 extends at least partially distally through a second guide slot 352 in the lower jaw 316b that is below and parallel to at least a portion of the flat extension 330s of the electrode 330. Further, planar member 344 engages with the flat extension 330s of the electrode 330. As such, energy transmitted through the conductive rod 340 from an energy source is conducted through the planar member 344 and to the electrode 330. One or more of the conductive rod 340, the conductive cap 342, the planar member 344, and/or the electrode 330 can have a non-conductive protective sleeve, similar to the sleeve 234, around at least a portion thereof that insulates the conductive pathway of the electrode 330 as it passes through the device 300.

The conductive rod 340 and the planar member 344 also act to linearly translate the electrode 330. Distal and proximal translation of the rod 340 causes corresponding translation of the distal-most end of the rod 340 with the conductive cap 342 through the first guide slot 350, which in turn translates the planar member 344 through the second guide slot 352. Translation of the planar member 344 results in linear translation of the electrode 330 between the retracted, bipolar position and the extended, monopolar position, as illustrated by arrows in FIG. 5D, effectively allowing the device 300 to switch between bipolar and monopolar modes. As the electrode 330 is translated distally, it can translate along the electrode channel 354, as illustrated in FIG. 5E.

When the electrode 330 is in the retracted position, it is in electrical and physical engagement with the bipolar electrode 319b such that the two electrodes 319b, 330 effectively operate as a unitary electrode. The electrode 330 forms part of a tissue contacting surface of the lower jaw 316b such that, upon grasping tissue by the jaws 316a, 316b and application of energy thereto in the bipolar mode of operation, the electrode 330 is part of the electrical path of the electrode 319b. The bipolar electrode 319b has a flat tissue contacting surface that corresponds to and extends opposite from the flat extension 330 in the lower jaw 316b. The distal hook 330t can be received into a notch 317 formed in the electrode 319b on the lower jaw 316b, as illustrated in FIG. 5E, such that the electrode 330 and the bipolar electrode 319b are generally flush with one another to form an uninterrupted tissue contacting and conductive surface on either side of the cutting element translation path 318p. The electrode 330 and the electrode 319b are thus electrically engaged in the retracted position through contact between the distal hook 330t and the notch 317. In the retracted position, the electrode 330 is therefore received entirely within the end effector 314. In the illustrated embodiment, the conductive rod 340 forms part of the bipolar electrical path of the bipolar electrodes 319a, 319b when the electrode 330 is engaged with the electrode 319b. For example, it acts as a primary source of energy to the end effector 314 by supplying energy to the electrode 319b through its engagement with the electrode 330. As such, the lower electrode 319b can thus act as the active electrode when the device is in the bipolar mode of operation, and the upper electrode 319a can act as the return electrode in the bipolar mode. When the electrode 330 is in the extended position in this embodiment, as discussed below, energy cannot be applied to the electrodes 319a, 319b because the conductive rod 340 is electrically isolated from the electrode 319b. However, in other embodiments, one or more other conductive members can be used to deliver energy to the electrodes 319a, 319b during bipolar tissue treatment such that various electrical connections to the rod 340 can be decoupled during bipolar treatment while still being able to apply energy to the end effector 314. In the illustrated embodiment, the electrodes 319b, 330 are made of the same material, however in other embodiments, different materials can be used.

When the conductive rod 340 is translated distally to move the electrode 330 into the extended, monopolar mode position, the electrode 330 is decoupled from electrical engagement with the electrode 319b such that the electrode 330 becomes electrically isolated from the bipolar electrical path. As such, the conductive rod 340 and the planar member 344 are also electrically isolated from the bipolar electrical path, and one or more of the conductive rod 340, conductive cap 342, planar member 344, guide slots 350, 352, and/or channel 354 are thus electrically insulated to help create electrical isolation in the extended position. As the electrode 330 is distally translated, the hook 330t moves distally out of the notch 317 and out of contact with the electrode 319b, breaking the electrical path formed between the electrodes 319b, 330. Any energy applied to the electrode 330 in this configuration is thus received in the monopolar mode of operation, bypassing the bipolar electrical pathway in the end effector 314. The electrode 330 can therefore be advanced linearly without any rotation thereof.

Distal and proximal translation of the conductive rod 340, which causes translation of the electrode 330, can be controlled by a variety of different mechanisms, similar to device 200. For example, it can be controlled through pivotal movement of the closure mechanism of the jaws 316a, 316b, through a separate pivotal grip or lever on the housing, through a sliding mechanism on the housing, through a knob positioned between the housing and the shaft 312, through one or more buttons or switches on the housing, etc.

Energy can be applied to the electrode 330 through a variety of different mechanisms, similar to device 200. In the illustrated embodiment, energy can be applied to the electrode 330 in the monopolar mode similar to energy applied to electrodes 319a, 319b in the bipolar mode. An energy actuator on the housing of the device 300 can be depressed, actuating delivery of energy through one or more conductive members from a generator and/or a power source.

In use, the device 300 can be used similar to devices 100, 200 when grasping tissue between the jaws 316a, 316b, transecting the grasped tissue, and applying energy thereto. The electrode 330 can initially be in the retracted position and engaged with the bipolar electrode 319b in a bipolar mode. When spot application of energy in the monopolar mode is desired, the electrode 330 can be translated from the retracted position to the extended position, as discussed above. As the electrode 330 extends distally, the electrode 330 can break its electrical connection with the electrode 319b such that the electrode 330 becomes electrically isolated from the bipolar electrical path. Once the electrode 330 is extended, energy can then be applied in the monopolar mode to target tissue by the tip 330t of the electrode 330 with the device 300. The electrode 330 can then be translated proximally to the retracted position again, causing the electrode 330 to retract into the end effector 314, reengage with the electrode 319b to form a tissue contacting surface therewith on the lower jaw 316b, and rejoin the bipolar electrical pathway. A user can then proceed with using device 300 in the bipolar mode.

The elongate shafts 212, 312 of devices 200, 300 are generally rigid shafts, however articulation of the elongate shaft and/or the end effector is possible while still allowing for an electrode to translate between a retracted position and an extended position to deliver monopolar energy therefrom even during articulation. FIGS. 6A-6G illustrate a surgical device 400 similar to devices 100, 200, 300 that has an electrode 430 that is translated between retracted and extended positions. The device 400 has an end effector 414, an elongate shaft 412, and a housing, which can be in the form of a handle (not shown). The shaft 412 extends distally from the housing and has the end effector 414 disposed on a distal end thereof, and it has at least one lumen extending therethrough for carrying mechanisms for actuating the end effector 414. The end effector 414 has a first upper jaw 416a and a second lower jaw 416b that is opposed thereto. The jaws 416a, 416b can grasp tissue therebetween, transect grasped tissue with a cutting element, and apply bipolar energy to grasped tissue through active and return electrodes 419a, 419b in the jaws 416a, 416b. In an embodiment in which the the housing is a handle, the handle includes a pivotal closure grip (not shown) that is pivoted to open and close upper and lower jaws 416a, 416b and one or more actuators (not shown) to cause transection of tissue grasped by the jaws 416a, 416b and delivery of energy to the end effector 414. Various gear(s), rack(s), drive screw(s), drive nut(s), motor(s), processor(s), conducting member(s), etc. can be disposed within the housing and/or the shaft 412 to translate actuation of the closure grip and various actuator(s) into actuation of functions on the end effector 414.

Furthermore, the shaft 412 is articulatable, using either manually actuated or powered mechanisms. An articulation joint 440 is disposed along the shaft 412 distal to the handle and proximal to the end effector 414 such that articulation of the end effector 414 relative to a longitudinal axis A2 of the shaft 414 proximal to the articulation joint 440 is possible. Thus, a longitudinal axis A3 of the end effector 414 can initially be coaxial with the longitudinal axis A2, and it can then intersect the longitudinal axis A2 at a non-zero angle during articulation. Articulation about joint 440 can be achieved in a variety of ways, such as through use of one or more articulation cables that extend along the shaft 412 and that can be linearly translated, axially rotated, etc., similar to the mechanisms discussed in U.S. Patent Pub. No. 2018/0271553, entitled "Surgical Instrument With Articulating And Rotating End Effector And Flexible Coaxial Drive," filed on Mar. 24, 2017 and incorporated by reference herein in its entirety.

Figure 6A:
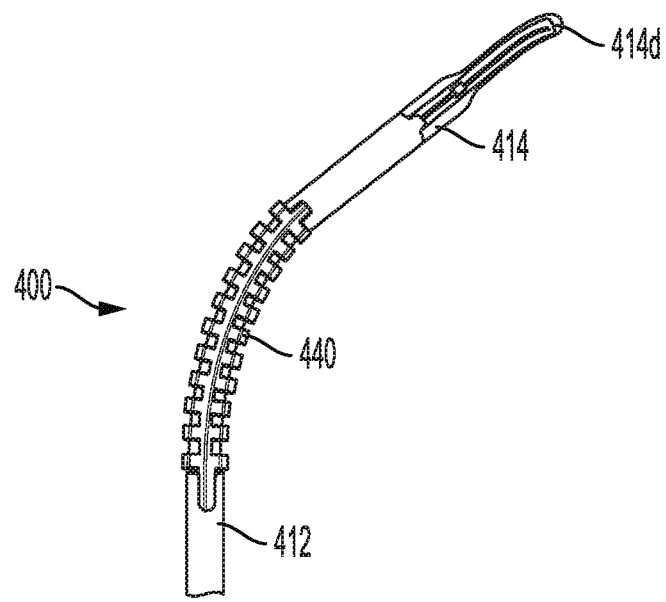
FIG. 6A is a top down view of an end effector and an articulatable shaft of another embodiment of a surgical device.
Figure 6B:
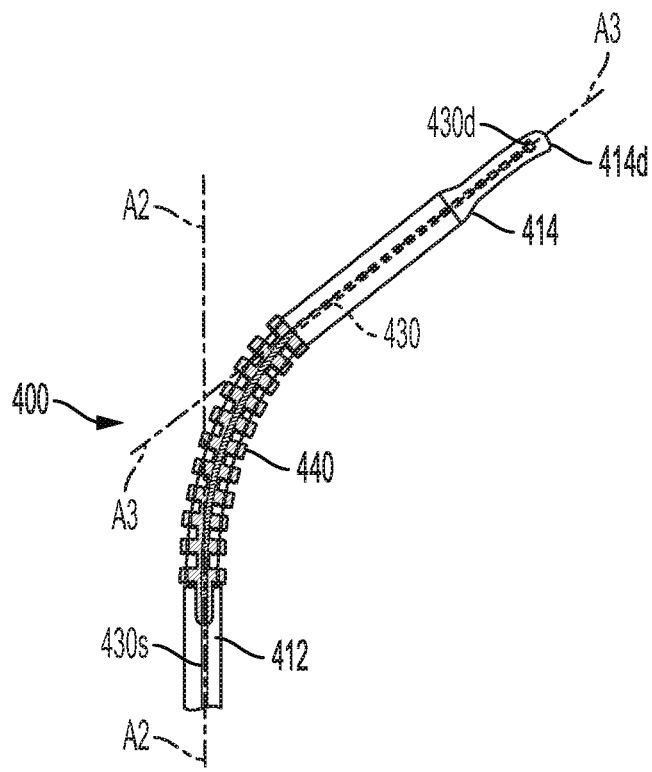
FIG. 6B is a partially-transparent top down view of the end effector of FIG. 6A.
Figure 6C:
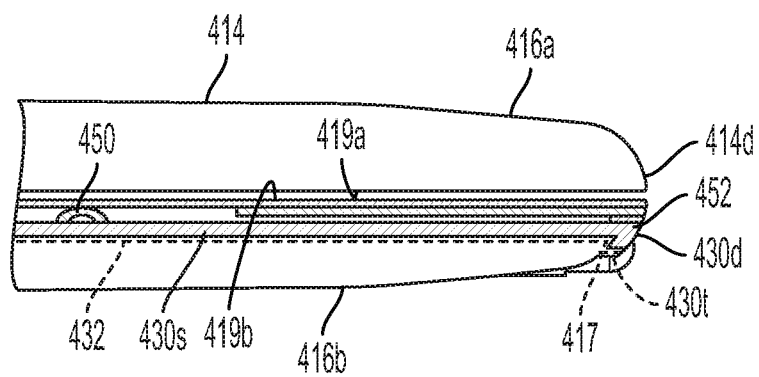
FIG. 6C is a partially-transparent side view of the end effector of FIG. 6A.
Figure 6D:
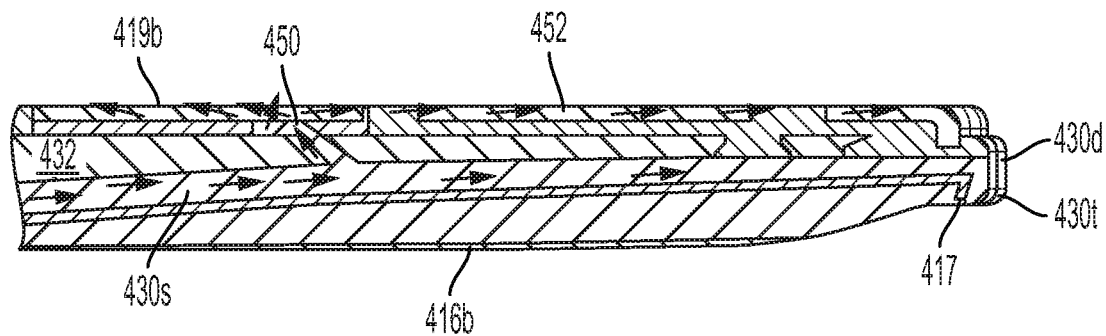
FIG. 6D is a cross-sectional side view of the end effector of FIG. 6A.
Figure 6E:
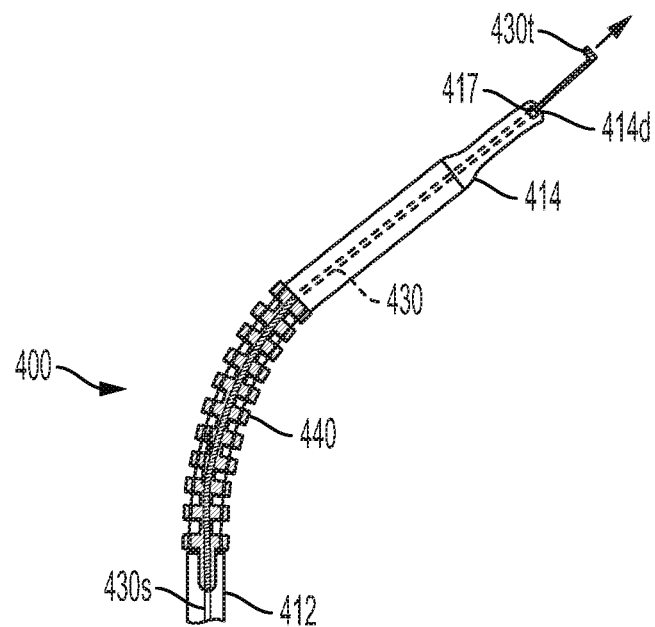
FIG. 6E is a partially-transparent top down view of the end effector of FIG. 6A with a conductive member in the process of translating distally.
Figure 6F:
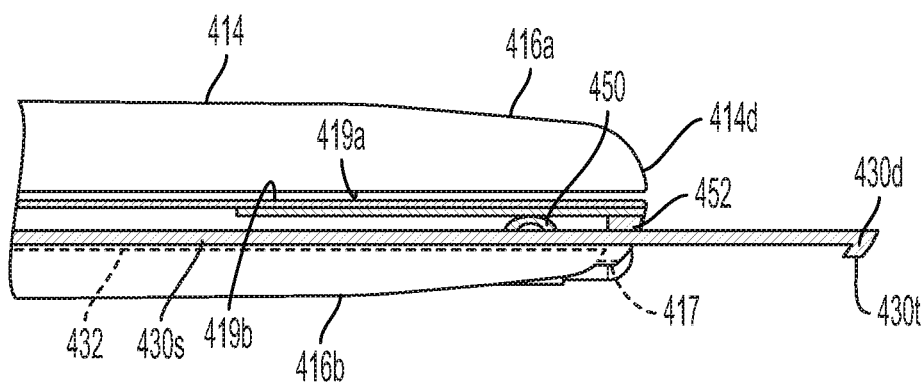
FIG. 6F is a partially-transparent side view of the end effector of FIG. 6A with the conductive member extended distally.
Figure 6G:
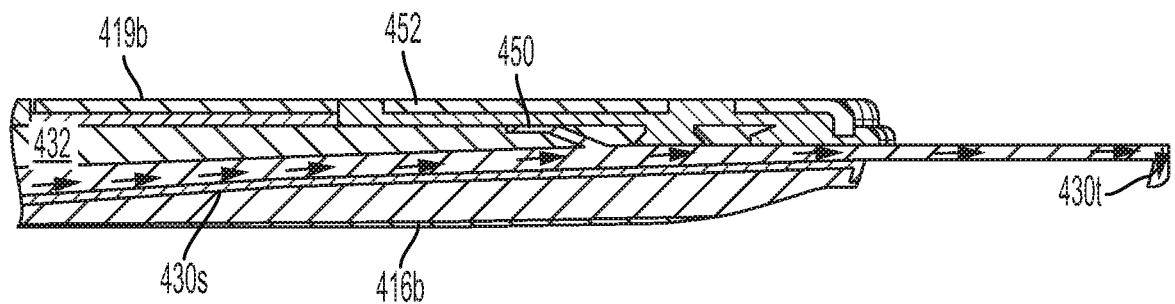
FIG. 6G is a cross-sectional side view of the end effector of FIG. 6A with the conductive member extended distally.

The electrode 430 extends longitudinally through at least a portion of the end effector 414 and the articulation joint 440 of the shaft 412. The electrode 430 is longitudinally translatable distally and proximally with respect to the end effector 414, and at least a portion of the electrode 430 is articulatable such that the electrode 430 can articulate with the joint 450 while still being longitudinally translatable with respect to the end effector 414. The electrode 430 can translate between a retracted position in which a majority of the electrode 430 is retracted within the end effector 414 and the shaft 412, as illustrated in FIGS. 6A-6D, and an extended position in which at least a distal end 430d of the electrode 430 protrudes distally beyond a distal end 414d of the end effector 414, as illustrated in FIGS. 6E-6G. In the retracted position, the electrode 430 engages with the bipolar electrical pathway of the end effector 414, similar to electrode 330. Upon distal translation of the electrode 430, the electrode 430 can act in the monopolar mode by electrically decoupling from engagement with a bipolar pathway, as discussed below and again as similar to electrode 330. Thus, upon distal translation of the electrode 430 and actuation of energy, the electrode 430 can be used to spot seal, coagulate, mark, cut, etc. tissue disposed adjacent to the distal end 414d of the end effector 414.

The electrode 430 has a general L shape with an elongate active rod 430s and a hook or bent tip 430t on a distal end thereof that extends at an approximately right angle thereto. The active rod 430s extends proximally through a longitudinal electrode channel 432 that extends through the second jaw 416b, and the active rod 430s itself is conductive and extends proximally through the articulation joint 440 and at least a portion of the shaft 412 to engage with one or more conductive members in the housing of the surgical device 400 for receiving energy therefrom. The active rod 430s acts as a source of electrical energy for the end effector 414 generally, including for the bipolar electrodes 419a, 419b as discussed below. At least a portion of the active rod 430s is flexible such that at least the portion of the rod 430s extending through the articulation joint 440 can articulate and flex with articulation of the joint 440 while still being able to conduct energy from the housing to the end effector 414. Furthermore, distal and proximal translation of the active rod 430s, discussed below, causes distal and proximal translation of the hook 430t and moves the electrode 430 between the retracted and extended positions. Thus, the rod 430s is sufficiently rigid to allow translation thereof while being flexible enough to allow translation even when the joint 440 has been articulated. The illustrated electrode 430 has a unitary body, however in other embodiments, one or more portions of the rod 430s and/or the hook 430t can be made from different materials and/or include different segments to allow sufficient flexibility in the articulation joint 440 and sufficient rigidity and conductivity during use. Additionally, the distal end 430d of the electrode 430 can have different shapes in different embodiments, such as a straight protruding tip.

The electrode 430 also can have a non-conductive protective sleeve, similar to sleeve 234, that insulates a majority of the active rod 430s as it passes through the device 400 and the shaft 412, while terminating proximal to the hook 430t. As such, the electrode 430 can have an exposed, electrically-active distal portion, and the sleeve can help protect various components within the device 400 from inadvertent electrical exposure. As such, the electrode channel 432 in the end effector 414 and the shaft 412 does not need to be electrically insulated. However, one or more portions of the end effector 414, the shaft 412, and/or the housing can be electrically insulated as desired to prevent energizing unintended areas.

In the retracted position, the hook 430t can be received in a distal tip notch 417 on a distal end of the second jaw 416b. As illustrated in FIGS. 6C and 6D, at least a portion, such as the distal end 430d of the electrode 230, can still be exposed to surrounding tissue when received within the channel 432 and the notch 417 such that surrounding tissue can be spot treated by the electrode 430 even in the retracted position. This allows a user to perform minor tissue modifications, such as limited spot coagulation, without having to extend the electrode. However, a majority of the electrode 430 is received into the end effector 414 and the shaft 412, and energy can be selectively terminated to the electrode 430 so that no energy is delivered thereto. This can avoid any accidental energy application during movement, treatment, etc. In other embodiments, the electrode can be withdrawn entirely into the end effector.

Furthermore, in the retracted position, the electrode 430 can be positioned in electrical engagement with the bipolar electrical pathway of the end effector 414. Specifically, the active rod 430s engages the lower electrode 419b, which is part of the bipolar electrical path of the jaws 416a, 416b, as illustrated in FIGS. 6C and 6D. Additionally, the active rod 430s is the primary source of energy for the end effector 414 by conveying energy from the housing and transmitting the energy to the lower electrode 419b in the retracted position, as represented by arrows in FIG. 6D. Energy is thus transmitted from the lower electrode 419b, through any tissue grasped by the end effector 414, and into the upper electrode 419a, which serves as a return electrode for the bipolar electrical pathway. Energy can then return proximally through the shaft 412, such as through one or more conductive members separate from the active rod 430s. Engagement between the active rod 430s and the lower electrode 419b can be created through a leaf spring 450 that is coupled to and protrudes from the active rod 430s. The active rod 430s extends through the channel 432 in the lower jaw 416b below the electrode 419b, and a proximal portion of the channel 432 has an open upper surface in communication with a lower surface of the electrode 419b. The leaf spring 450 extends through the open upper surface of the channel 432 along the proximal portion thereof and into slidable engagement with the lower surface of the electrode 419b when the electrode 430 is in the retracted position. Thus, energy applied to the active rod 430s can pass through the leaf spring 450 and into the electrode 419b to create the active electrode of the bipolar electrical pathway of the jaws 416a, 416b. As illustrated in FIG. 6D, energy can also pass through the entirety of the electrode 430, thus allowing for spot treatment of tissue using the distal end 430d of the electrode 430 (preferably when tissue is not grasped by the end effector 414). In the illustrated embodiment, the distal end 430d of the electrode 430 is thus always active when energy is being applied to the electrodes 419a, 419b, such as to grasped tissue. However, application of energy to the end effector 414 can be restricted entirely to prevent any accidental tissue contact with the active distal end 430d of the electrode 430, such as during movement of the end effector 414.

As the electrode 430 is translated distally into the extended position, the leaf spring 450 slides distally along the lower surface of the electrode 419b until it reaches a distal portion of the channel 432 with an insulating layer 452 formed along at least an upper surface thereof. The distal portion of the channel 432 thus does not communicate directly with the bipolar electrode 419b, unlike the proximal portion of the channel 432, and is instead electrically isolated therefrom. As the leaf spring 450 contacts the upper insulating layer 452, the spring 450 is compressed entirely into the distal portion of the channel 432 and out of contact with the bipolar electrode 419b, as illustrated in FIGS. 6F and 6G. Because the upper insulating layer 452 acts as an electrically isolating layer between the leaf spring 450 and the electrode 419b, energy applied to the active rod 430s from the handle is not conducted to the electrode 419b when the leaf spring 450 is in the distal portion of the channel 432. Energy is consequently only conducted along the electrode 430 itself, as illustrated by arrows in FIG. 6G. Thus, distal translation of the electrode 430 prevents energy from being applied to the bipolar electrodes 419a, 419b while still allowing energy to be applied through the electrode 430 in the monopolar mode. In such a monopolar mode, the hook 430t of the electrode 430 protrudes distally from the end effector 414, and energy transmitted to the active rod 430s can be applied to tissue adjacent to the hook 430t of the electrode 430 while bypassing the electrodes 419a, 419b entirely. Subsequent proximal translation of the active rod 430s can reform the engagement between the leaf spring 450 and the bipolar electrode 419b to return to the bipolar mode. Thus, the active rod 430s can deliver energy across the articulation joint 440 in both monopolar and bipolar modes, articulate with the joint 440, and translate the electrode 430 distally and proximally while limiting the need for additional components to be passed through the articulation joint 440.

Distal and proximal translation of the active rod 430s, which causes translation of the electrode 430, can be controlled by a variety of different mechanisms, similar to devices 200, 300. For example, it can be controlled through pivotal movement of the closure mechanism of the jaws 416a, 416b, through a separate pivotal grip or lever on the housing, through a sliding mechanism on the housing, through a knob positioned between the housing and the shaft 412, through one or more buttons or switches on the handle, etc.

Energy can be applied to the electrode 430 through a variety of different mechanisms, as well, similar to devices 200, 300. In the illustrated embodiment, energy can be applied to the electrode 430 in the monopolar mode similar to applying energy to electrodes 419a, 419b in the bipolar mode through the active rod 430s. An energy actuator on the housing of the device 400 can be depressed, actuating delivery of energy through one or more conductive members from a generator and/or a power source to the active rod 430s.

The device 400 can be used in a manner similar to devices 100, 200, 300 when grasping tissue between the jaws 416a, 416b, transecting the grasped tissue, and applying energy thereto. The electrode 430 can be initially in the retracted position and maintain an electrical connection with the bipolar electrode 419b to provide energy thereto in a bipolar mode. The end effector 414 with the electrode 430 can be selectively articulated about the joint 440 on the shaft 412. Minor spot applications of monopolar energy can be conducted by the distal end 430d of the electrode 430 without extending it from the end effector 414. However, when more substantive spot applications of energy are desired, the electrode 430 can be translated from the retracted position to the extended position, as discussed above. As the electrode 430 extends distally, the electrode 430 can break its electrical connection with the bipolar electrode 419b such that the electrode 430 is electrically isolated from the bipolar electrical path. Once the electrode 430 is extended distally, monopolar energy can then be applied to target tissue by the tip 430t of the electrode 430 with the device 400 in the monopolar mode. The electrode 430 can then be translated proximally to the retracted position again, causing the electrode 430 to retract into the end effector 414, reengage its electrical connection with the bipolar electrode 419b, and allow energy to be applied to the bipolar electrical pathway again. A user can then proceed with using device 400 in the bipolar mode.

In other embodiments, a variety of different components in the end effector can be used to extend and retract a monopolar electrode and deliver energy thereto, limiting the need for additional components to be added thereto. FIGS. 7A-7J illustrate a surgical device 500 similar to surgical devices 100, 200, 300, 400. While it has a monopolar electrode 530 that is translated between retracted and extended positions, the electrode 530 is translated by and supplied with energy through a cutting element 518 thereof. The device 500 has an end effector 514, an elongate shaft 512, and a housing that can be in the form of a handle (not shown). The shaft 512 extends distally from the housing and has the end effector 514 disposed on a distal end thereof, and it has at least one lumen extending therethrough for carrying mechanisms for actuating the end effector 514. The end effector 514 has a first upper jaw 516a and a second lower jaw 516b that is opposed thereto. The jaws 516a, 516b can grasp tissue therebetween, transect grasped tissue with the cutting element 518, and apply energy in a bipolar mode to grasped tissue through active and return electrodes 519a, 519b in the jaws 516a, 516b. The housing includes a pivotal closure grip (not shown) that is pivoted to open and close upper and lower jaws 516a, 516b and one or more actuators (not shown) to cause transection of tissue grasped by the jaws 516a, 516b and delivery of energy to the end effector 514. Various gear(s), rack(s), drive screw(s), drive nut(s), motor(s), processor(s), conducting member(s), etc. can be disposed within the handle and/or the shaft 512 to translate actuation of the closure grip and various actuator(s) into actuation of functions on the end effector 514.

The cutting element 518 translates distally and proximally along a cutting channel 524 that extends along a central longitudinal axis A4 of the end effector 514 and into both the upper and lower jaws 516a, 516b through the electrodes 519a, 519b. When transecting and sealing tissue, the cutting element 518 transects tissue through a full cutting stroke by moving from a proximal end to a distal end of the cutting channel 524, and the electrodes 519a, 519b apply energy in the bipolar mode to grasped tissue on either side of the cutting channel 524 to seal tissue that is transected by the cutting element 518. The cutting element 518 has a distal cutting head or tip 520 and a proximal cutting shaft 522. The cutting head 520 is a rectangular member with a distal cutting surface 520d and a proximal engagement surface 520p. The cutting surface 520d extends between the upper and lower jaws 516a, 516b in the cutting channel 524 to transect tissue as it moves distally therethrough, and the proximal engagement surface 520p extends into the cutting channel 524 on the lower jaw 516b. The cutting element 518 also has a proximal cutting shaft 522 that extends proximally from the cutting head 520 into the shaft 512. As such, the cutting head 520 translates distally and proximally through the cutting channel 524 due to distal and proximal translation of the cutting shaft 522.

Additionally, the monopolar electrode 530 extends longitudinally through at least a portion of the end effector 514 and is longitudinally translatable distally and proximally with respect thereto. The electrode 530 can translate between a retracted position in which a majority of the electrode 530 is retracted within the end effector 514, as illustrated in FIGS. 7A-7C and 7J, and an extended position in which at least a distal end 530d of the electrode 530 protrudes distally beyond a distal end 514d of the end effector 514, as illustrated in FIG. 7F-7I. Upon distal translation of the electrode 530 and actuation of energy, as discussed below, the electrode 530 can be used to spot seal, coagulate, mark, cut, etc. tissue disposed adjacent to the distal end 514d of the end effector 514.

The electrode 530 has a general J or L shape with an elongate rod 530s and a hook or bent tip 530t on a distal end thereof that extends toward the upper jaw 516a. The rod 530s extends between a contact post 531a and a return post 531b through a longitudinal electrode groove 532 that extends along a bottom surface of the second jaw 516b beneath and parallel to the cutting channel 524. The contact and return posts 531a, 531b extend from the rod 530s toward the upper jaw 516a into the cutting channel 524 in the lower jaw 516b.

The electrode 530 also has a non-conductive protective sleeve 534 that insulates a majority of the electrode rod 530s as it passes through the groove 532 in the lower jaw 516b and the return post 531b and terminating proximal to the hook 530t and the contact post 531a. As such, the electrode 530 has an exposed, electrically-active distal portion, including the contact post 531a, while the sleeve 534 can help protect various components within the end effector 514 and any secondary tissue from inadvertent electrical exposure.

When the electrode 530 is in the retracted position and the device 500 is operating in a bipolar mode, the hook 530t of the electrode 530 can be received in a distal tip notch 517 on a distal end of the second jaw 516b. At least a portion of the electrode 530, such as a corner 530c, can still be exposed to surrounding tissue when the hook 530t is received in the groove 532 and the notch 517 such that surrounding tissue can be spot treated by the electrode 530 even in the retracted position and can receive energy from the cutting element 518 for such spot treatment, as described below.

Figure 7A:
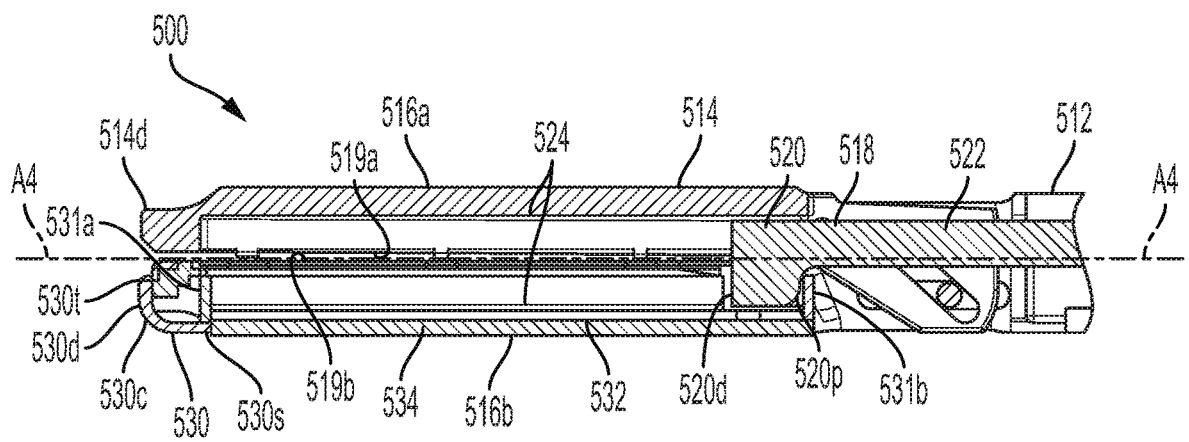
FIG. 7A is a cross-sectional side view of an end effector and a shaft of another embodiment of a surgical device.
Figure 7B:
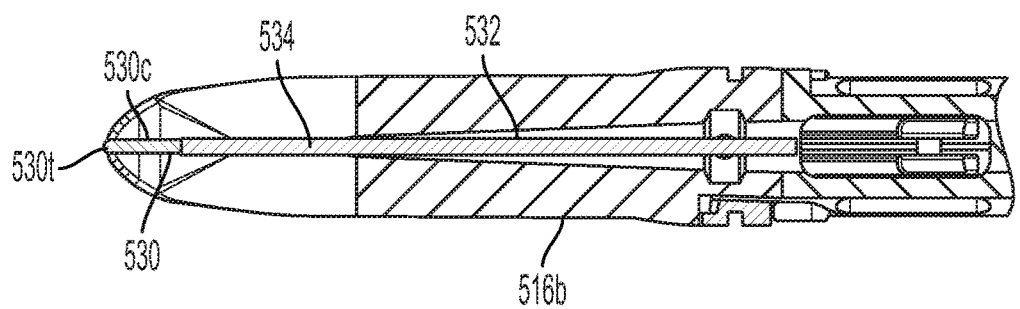
FIG. 7B is a bottom up view of a lower exterior surface of the end effector of FIG. 7A.
Figure 7C:
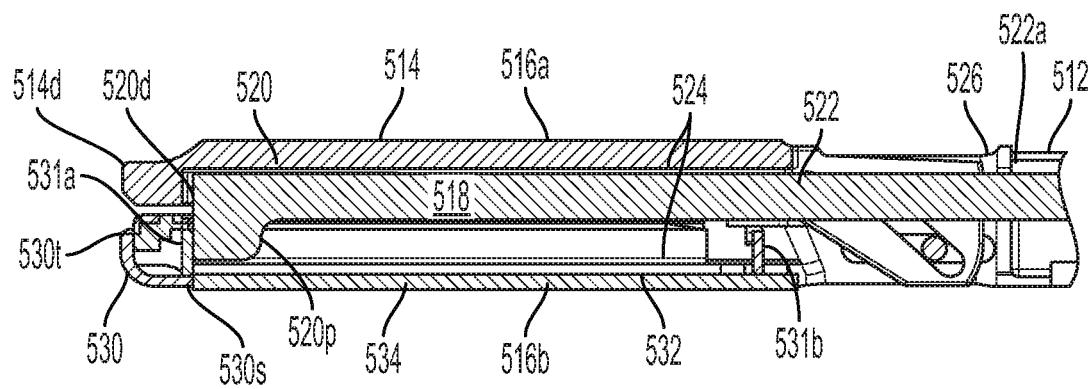
FIG. 7C is a cross-sectional side view of the end effector of FIG. 7A with a cutting element translated distally through a full cutting stroke.
Figure 7D:
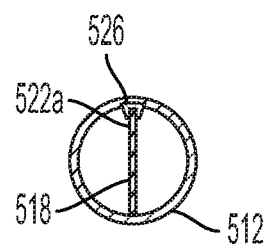
FIG. 7D is a cross-sectional view along the shaft toward the end effector of the surgical device of FIG. 7A with a knife stop in obstructing engagement with the cutting element.
Figure 7E:
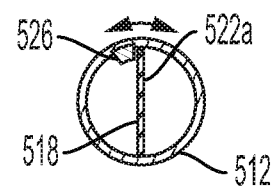
FIG. 7E is a cross-sectional view along the shaft toward the end effector of the surgical device of FIG. 7A with the knife stop rotated counterclockwise out of obstructive engagement with the cutting element.

Also while in the retracted position, the contact post 531a extends into the cutting channel 524 proximal to a distal terminal end thereof, and the return post 531b extends into the cutting channel 524 at a proximal terminal end. The contact and return posts 531a, 531b are positioned in the cutting channel 524 at distal and proximal ends of a full cutting stroke of the cutting element 518 during a bipolar operation when the electrode 530 is retracted. The proximal engagement surface 520p of the cutting head 520 contacts the return post 531b in an initial cutting position before extending through the cutting channel 524 to transect tissue, as illustrated in FIG. 7A. At the end of a full cutting stroke as illustrated in FIG. 7C, the distal cutting surface 520d contacts the contact post 531a after passing distally through the cutting channel 524 and cutting tissue grasped between the two jaws 516a, 516b. Additionally, spot treatment of tissue with energy in the monopolar mode is possible through the exposed corner portion 530c of the electrode when the cutting element 518 is in such a distally engaged position, as illustrated in FIG. 7C. Energy can be applied to the cutting element 518, which is a conductive member. Because the cutting element 518 is in contact with the contact post 531a, which is also a conductive member, energy is thus conducted through the cutting element 518 and into the exposed corner 530c of the electrode 530 through the contact post 531a. Minor monopolar treatment can thus be performed without extending the electrode 530. A spring-biased knife stop 526 is positioned on an upper surface of the shaft 512 at a distal end thereof where the shaft 512 and the end effector 514 operably engage. The knife stop 526 obstructs distal translation of the cutting element 518 at the end of a full cutting stroke by engaging a protrusion 522a on the cutting shaft 522 of the cutting element 518. The protrusion 522a is positioned proximally to the knife stop 526 along the cutting shaft 522 in the elongate shaft 512 of the device 500 when the cutting element 518 is in the initial, pre-cutting stroke position in FIG. 7A. The protrusion 522a is positioned at a proximal distance from the knife stop 526 such that, as the cutting element 518 translates distally during a cutting stroke, the protrusion 522a encounters and is distally obstructed by the knife stop 526 at the end of the cutting stroke when the distal cutting surface 520d contacts the contact post 531a, as illustrated in FIGS. 7C and 7D. The knife stop 526 is rotationally positioned on the shaft 512 such that clockwise and counterclockwise rotation of the knife stop 526 about the axis A4 is possible to allow the cutting element 518 to proceed past a full cutting stroke, as discussed below. However, the knife stop 526 is spring biased to remain in an obstructive position with the cutting element 518 such that, without external force being applied thereto, the knife stop 526 prevents the cutting element 518 from extending further distally at the end of a complete cutting stroke.

Figure 7F:
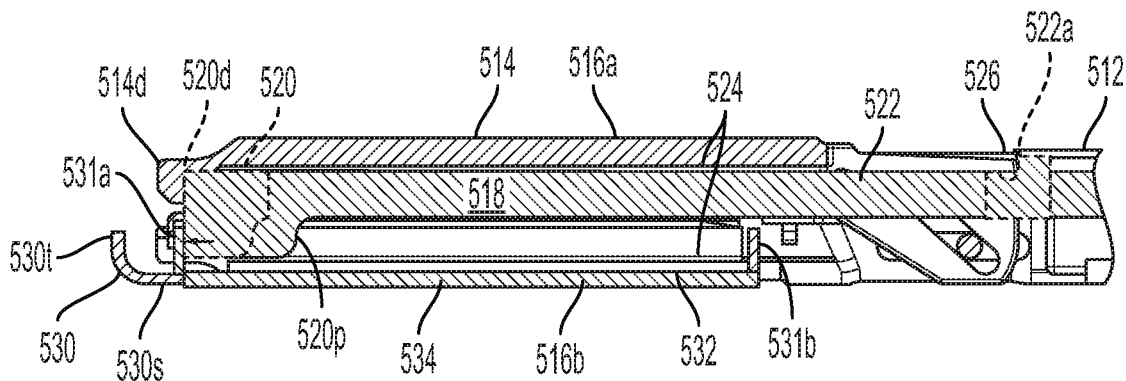
FIG. 7F is a cross-sectional side view of the end effector of FIG. 7A with the cutting element and a conductive member extended distally.
Figure 7G:
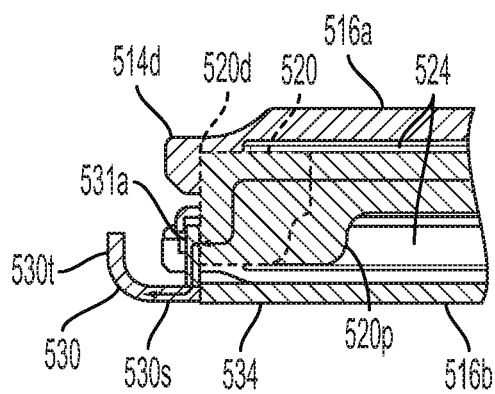
FIG. 7G is a cross-sectional side view of a distal portion of the end effector of FIG. 7A with the cutting element and the conductive member extended distally.
Figure 7H:
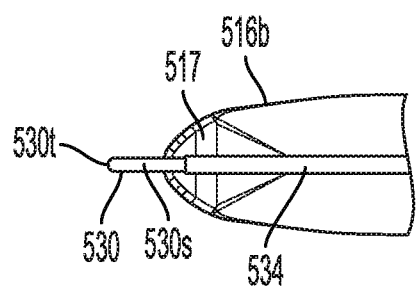
FIG. 7H is a bottom up view of the lower exterior surface of a distal portion of the end effector of FIG. 7A with the conductive member extended distally.

To extend the electrode 530 distally for use in spot treatment and to transition the device 500 to a monopolar mode, the cutting element 518 is first actuated to extend it to a full cutting stroke, as discussed above and illustrated in FIG. 7C. When the protrusion 522a of the cutting element 518 contacts the knife stop 526, the knife stop 526 can be rotated clockwise or counterclockwise out of obstructive engagement with the protrusion 522a, as illustrated by arrows in FIG. 7E. Rotation of the knife stop 526 can be achieved through a variety of mechanisms, such as a thumb switch on the housing or a rotational knob on the shaft 512. When the knife stop 526 is rotated out of engagement, the cutting element 518 can be extended distally past a full cutting stroke. As such, the distal cutting surface 520d contacts the contact post 531a and translates the contact post 531a distally by applying a linear distal force thereto, which distally translates the entire electrode 530 into the extended position, as illustrated by an arrow in FIG. 7F. The cutting surface 520d contacts and is obstructed by the distal terminal end of the cutting channel 524 when the electrode 530 is fully distally translated, and the cutting element is held in a distal-most engagement position with the contact post 531a during monopolar treatment. The return post 531b is translated distally away from a proximal terminal end of the cutting channel 524 with overall distal translation of the electrode 530, as illustrated in FIG. 7F. Energy is then applied to the cutting element 518, which is in contact with the contact post 531a. As illustrated by an arrow in FIG. 7G, energy is thus conducted through the cutting element 518 and into the electrode 530 through the contact post 531a. Monopolar treatment can then be performed on tissue adjacent to the hook 530t. To apply energy to the electrode 530 either in the extended position or in the retracted position for minor spot treatment, the cutting element 518 is thus extended distally through the jaws 516a, 516b and into contact with the contact post 531a, which can occur when the jaws 516a, 516b are in the closed position.

Figure 7I:
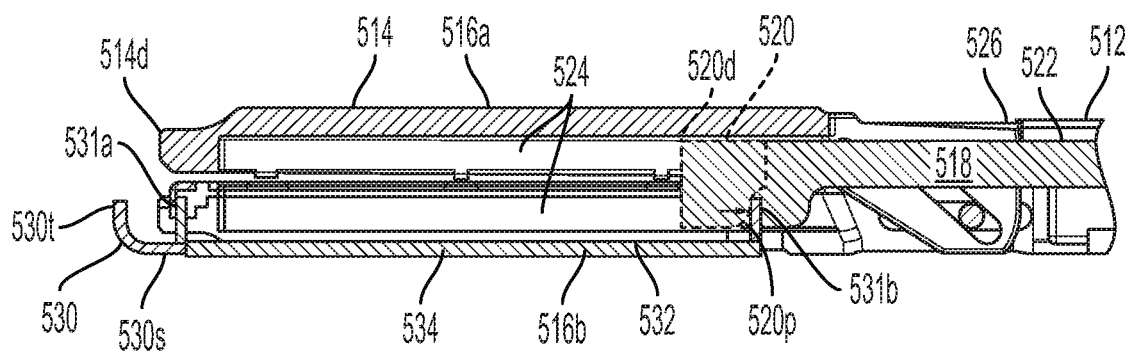
FIG. 7I is a cross-sectional side view of the end effector of FIG. 7A with the cutting element retracted proximally.
Figure 7J:
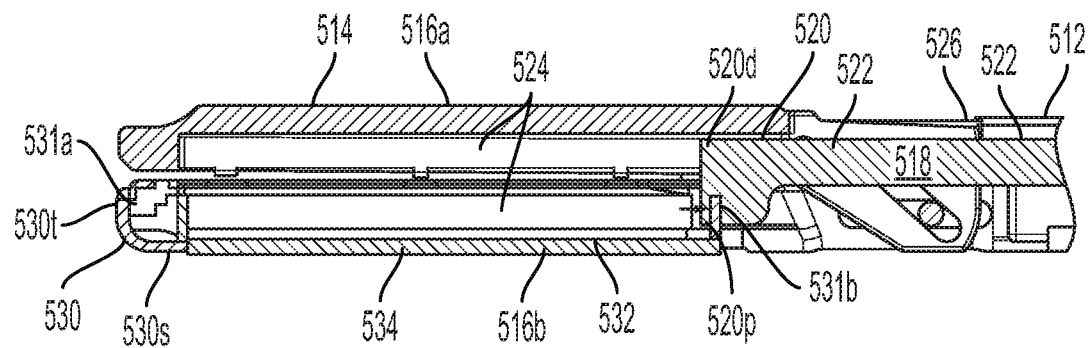
FIG. 7J is a cross-sectional side view of the end effector of FIG. 7A with the cutting element and the conductive member retracted proximally.

To retract the electrode 530 and return the device 500 to the bipolar mode, the cutting element 518 is retracted proximally, as illustrated in FIG. 7I. As the protrusion 522a translates proximally past the knife stop 526, the knife stop 526 rotates back into obstructive engagement with the cutting element 518 to prevent subsequent distal translation of the electrode 530 by the cutting element 518 without a new rotational force being applied thereto. As the cutting element 518 translates proximally, the proximal engagement surface 520p of the cutting head 520 contacts the return post 531b in its distal, extended position in the cutting channel 524. The proximal engagement surface 520p translates the return post 531b proximally to the proximal terminal end of the cutting channel 524 as the cutting element 518 returns to its initial, pre-cutting stroke proximal position. As the return post 531*b* is translated proximally, it in turn translates the entire electrode 530 proximally to the retracted position, as illustrated in FIG. 7J. In another embodiment, the cutting element 518 can be used to extend the electrode 530 as described above, however the electrode 530 can be returned to the retracted position through one or more mechanisms, such as magnets in the lower jaw 516*b*, spring biasing, etc. Thus, distal translation of the monopolar electrode 530 and application of energy thereto can be accomplished through use of the cutting element 518 without having to add a plurality of additional components to the device 500.

Distal and proximal translation of the cutting element 518 can be controlled by a variety of different mechanisms, similar to devices 200, 300, 400. A cutting actuator on the housing can be used to cause transection of tissue grasped in the jaws 516*a*, 516*b* in the bipolar mode, and it can also be used to cause distal extension of the cutting element 518 when transitioning to the monopolar mode, such as having a first range of actuation motion for tissue transection and a second range of actuation motion for continued distal translation into the monopolar mode. However, a variety of other mechanisms are possible, such as through a separate pivotal grip, lever, or trigger on the housing, through a sliding mechanism on the housing, through a knob on the housing or the shaft 412, through one or more buttons or switches on the handle, etc.

Energy can be applied to the electrode 530 through the cutting element 518 by a variety of different mechanisms, similar to devices 200, 300, 400. For example, energy can be applied to the cutting element 518 in the monopolar mode similar to energy being applied to electrodes 519*a*, 519*b* in the bipolar mode, such as through the same conductive members. However, in other embodiments, one or more separate conductive members can be present in the housing and/or the shaft 512, some combination of the two can be used, etc. In some embodiments, energy can be prevented from being applied to the electrodes 519*a*, 519*b* when the electrode 530 is extended. However, in other embodiments, energy can be applied to the electrodes 519*a*, 519*b* even when the electrode 530 is extended because the jaws 516*a*, 516*b* are in the closed position and thus any energy applied to the electrodes 519*a*, 519*b* can be limited to the end effector 514 and/or other components of the device 500 rather than interfering with monopolar treatment. Actual actuation of energy to the cutting element 518 can also be triggered in a variety of ways, similar to the mechanisms discussed above. For example, an energy actuator on the handle of the device 500 can be depressed, actuating delivery of energy through one or more conductive members from a generator and/or a power source to the cutting element 518.

The device 500 can be used in a manner similar to devices 100, 200, 300, 400 when grasping tissue between the jaws 516*a*, 516*b*, transecting the grasped tissue, and applying energy thereto. The electrode 530 can initially be in the retracted position, and minor spot treatment of tissue can be performed by actuating the cutting element 518 through a full cutting stroke and applying energy thereto while the cutting element 518 is positioned distally into contact with the contact post 534*a* of the electrode 530. When a more complete spot application of energy is desired, the electrode 530 can be translated from the retracted position to the extended position by rotating the knife stop 526 out of obstructive engagement with the cutting element 518 and advancing the cutting element 518 distally to contact and force the contact post of the electrode 530 distally. Once the electrode 530 is fully extended and the device 500 is in monopolar mode, energy can be applied to target tissue by the hook 530*t* of the electrode 530 by applying energy to the cutting element 518, which conducts the energy through the contact post 534*a* and into the electrode 530. The electrode 330 can then be translated proximally to the retracted position again by retracting the cutting element 518, which engages the return post 534*b* on the electrode 530 and translates proximally. A user can then proceed with using the device 500 in the bipolar mode.

Figure 8:
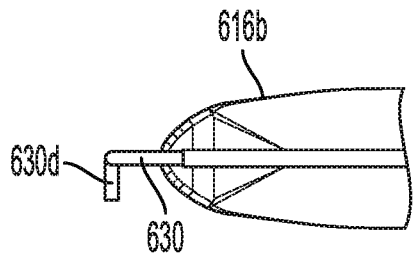
FIG. 8 is a bottom up view of a lower exterior surface of a distal portion of another embodiment of a surgical device.
Figure 9:
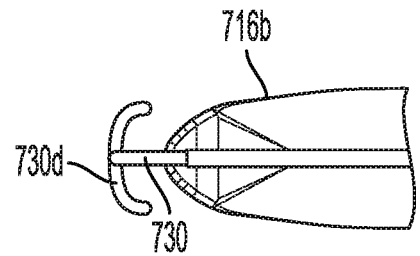
FIG. 9 is a bottom up view of a lower exterior surface of a distal portion of another embodiment of a surgical device.

Furthermore, while hook 530*t* is in the form of a rod extending toward the upper jaw 516*a*, the distal end of the electrode is not limited thereto. For example, FIGS. 8 and 9 illustrate additional embodiments of distal ends of monopolar electrodes on end effectors. FIG. 8 illustrates a distal end 630*d* of an electrode 630, similar to electrode 530, that extends through a lower jaw 616*b*, similar to lower jaw 516*b*. The distal end 630*d* is in the form of a hook or tip that extends perpendicular to an elongate rod of the electrode 630 and parallel to a plane passing through a tissue contacting surface of the lower jaw 616*b*, resembling a horizontal L. FIG. 9 illustrates a distal end 730*d* of an electrode 730, similar to electrode 530, that extends through a lower jaw 716*b*, similar to lower jaw 516*b*. The distal end 730*d* is in the form of a proximally-curved T with curved arms that extend in a plane parallel to a plane passing through a tissue contacting surface of the lower jaw 716*b*.

Figure 10A:
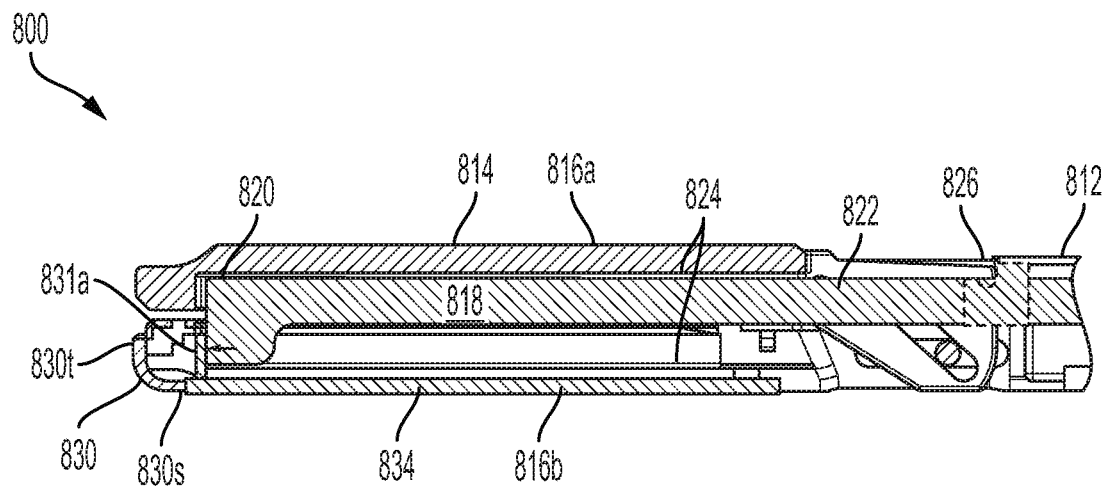
FIG. 10A is a cross-sectional side view of an end effector and a shaft of another embodiment of a surgical device.
Figure 10B:
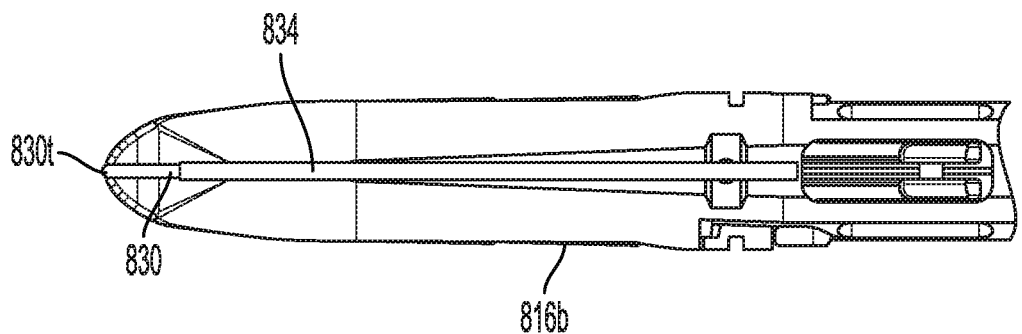
FIG. 10B is a bottom up view of a lower exterior surface of the end effector of FIG. 10A.

While the electrode 530 is distally extendable, in some embodiments a monopolar electrode can be fixed in a retracted position such that use of the electrode is limited to minor spot treatment by the exposed portion thereof. FIGS. 10A and 10B illustrate a device 800, similar to device 500, that has an end effector 814, an elongate shaft 812, and a handle (not shown). The end effector 814 has a first upper jaw 816*a* and a second lower jaw 816*b* with electrodes disposed therein. Similar to end effector 514, the end effector 814 has a cutting element 818 with a distal cutting head 820 and a proximal cutting shaft 822. The cutting head 820 can translate distally and proximally in a cutting channel 824 through the end effector 814, and the proximal cutting shaft 822 is obstructed by a knife stop 826 at a completion of a full cutting stroke.

Furthermore, an electrode 830, similar to electrode 530, extends through the lower jaw 816*a* and has an electrode rod 830*s* and a hook or bent tip 830*t* on a distal end thereof that extends toward the upper jaw 816*a*. The hook 830*t* is exposed to surrounding tissue during bipolar operation of the device 800 such that surrounding tissue can be spot treated by the electrode 830 without distally extending the electrode 830. The rod 830*s* extends proximally from a contact post 831*a* that extends at approximately n right angle from the rod 830*s* toward the upper jaw 816*a* into the cutting channel 824. The contact post 531*a* is positioned in the cutting channel 824 at a distal end of a full cutting stroke of the cutting element 818. The electrode 830 does not have a return post, unlike electrode 530, because the electrode 830 is not translated. A non-conductive protective sleeve 834 insulates a majority of the electrode rod 830*s* as it passes through the lower jaw 816*b*, while the hook 830*t* and the contact post 831*a* remain uninsulated and exposed.

Thus, at the end of a full cutting stroke, the cutting head 820 contacts the contact post 831*a* after passing distally through the cutting channel 824 and cutting tissue grasped between the two jaws 816*a*, 816*b*, as illustrated in FIG. 10A. Minimal spot treatment of tissue with monopolar energy can then be performed by the hook 830*t* when the cutting element 818 is in this fully extended distal position. As such, energy can be applied to the cutting element 818, which then conducts the energy through the contact post 831a and into the exposed portion of the hook 830t, as indicated by an arrow in FIG. 10A. The electrode 830 is not configured to be extended distally such that, after application of monopolar energy to tissue adjacent to the exposed portion of the hook 830t, the cutting element 818 can be retracted proximally and the device 800 can continue to be operated in a bipolar mode.

Figure 11A:
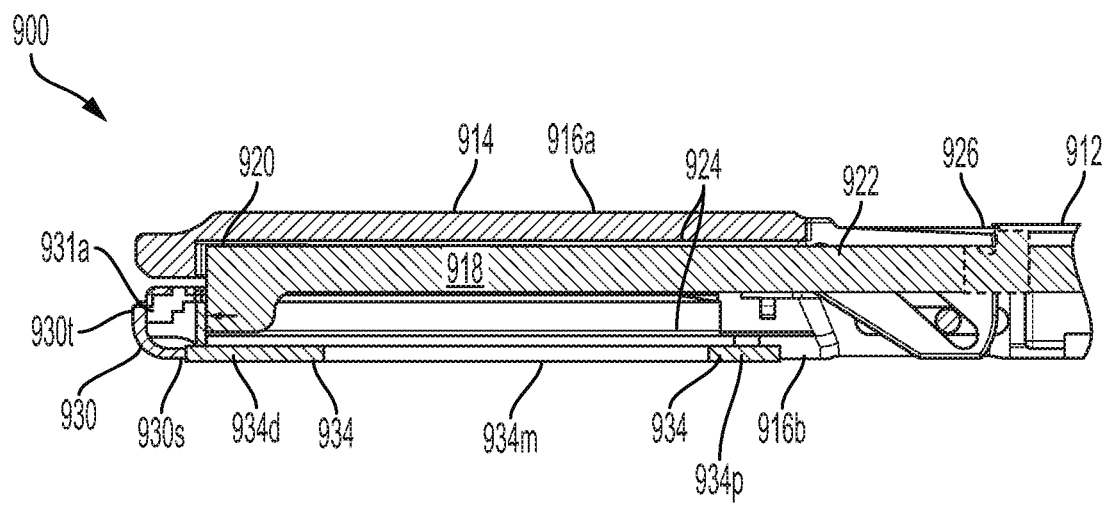
FIG. 11A is a cross-sectional side view of an end effector and a shaft of another embodiment of a surgical device.
Figure 11B:
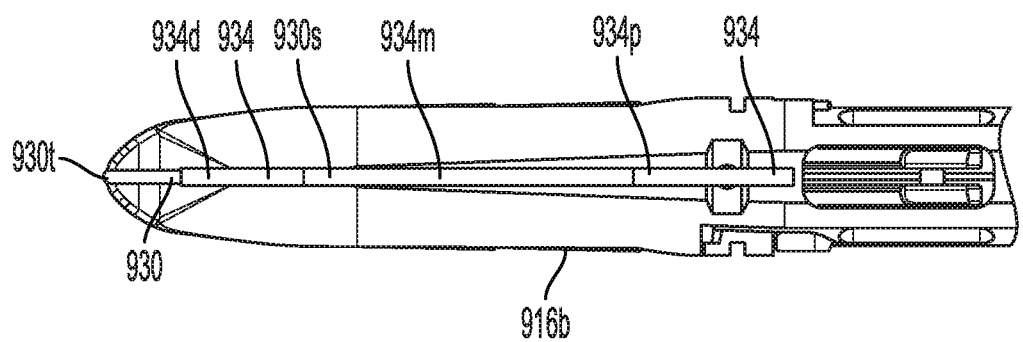
FIG. 11B is a bottom up view of a lower exterior surface of the end effector of FIG. 11A.

Additionally, while a comparatively small portion of the electrode 830 is exposed in its fixed, retracted position of the device 800, a larger portion of a monopolar electrode can be exposed in a retracted position in other embodiments, such as for use during liver procedures. FIGS. 11A and 11B illustrate a device 900, similar to device 800, that has an end effector 914, an elongate shaft 912, and a handle (not shown). The end effector 914 has a first upper jaw 916a and a second lower jaw 916b with electrodes disposed therein. Similar to end effector 914, the end effector 914 has a cutting element 918 with a distal cutting head 920 and a proximal cutting shaft 922 extending proximally therefrom that is obstructed by a knife stop 926 at completion of a full cutting stroke in the end effector 914.

The end effector 914 also has an electrode 930, similar to electrode 830, that extends through the lower jaw 916a. The electrode 930 has an electrode rod 930s and a hook or bent tip 930t on a distal end thereof, and the rod 930s extends proximally from a contact post 931a. The contact post 931a extends at approximately a right angle from the rod 930s toward the upper jaw 916a into the cutting channel 924. It is positioned in the cutting channel 924 at a distal end of a full cutting stroke of the cutting element 918, similar to device 800. As such, the distal cutting head 920 contacts the contact post 931a at the end of the stroke. Energy can thus be applied to the electrode 930 through the cutting element 918 and the contact post 931a, similar to the electrode 830 and as indicated by an arrow in FIG. 11A. However, a non-conductive protective sleeve 934 insulates the distal tip 930t and distal and proximal portions 934d, 934p of the electrode rod 930s as it passes through the lower jaw 816b, while a middle portion 934m of the electrode rod 930s and the contact post 831a remain uninsulated and the middle portion 934m remains exposed to surrounding tissue, as illustrated in FIGS. 11A and 11B. As such, when energy is applied to the electrode 930, monopolar treatment of tissue occurs to tissue positioned adjacent to a bottom external surface of the lower jaw 916b where the electrode rod 930s remains exposed to tissue rather than at the hook 930t. Such a configuration allows for coagulation and treatment of a larger tissue surface than treatment through a distal end of the end effector 914 would allow. However, in other embodiments, a monopolar electrode can be provided that has both an exposed middle portion of an electrode rod and an exposed distal end or hook thereof.

The various housings and/or handles of the devices discussed above can each be incorporated into one or more robotic surgical systems such that robotic surgical control is possible for each of the end effectors discussed herein. All of the devices disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It is preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:
1. A surgical device, comprising:
a housing;
an elongate shaft extending from the housing and defining a first longitudinal axis;
an end effector extending distally from the elongate shaft, the end effector having first and second jaws, at least one of which is movable between a spaced position for receiving tissue and a clamped position for engaging tissue, the first and second jaws being configured to conduct energy through tissue grasped therebetween; and
a conductive rod extending through the elongate shaft and through the first jaw, the conductive rod being axially translatable along the first longitudinal axis between a proximal-most position in which the conductive rod contacts an electrode on the first jaw to form a tissue-contacting surface and an electrical pathway of the first jaw to create a closed bipolar energy circuit allowing the first and second jaws to conduct energy through tissue grasped therebetween, and a distal-most position in which the conductive rod is electrically isolated from the electrode on the first jaw and extends distally from the end effector to allow energy to be conducted through the conductive rod to tissue adjacent thereto.

2. The surgical device of claim 1, further comprising an articulation joint on a distal end of the elongate shaft, the articulation joint being configured to articulate the end effector relative to the first longitudinal axis of the elongate shaft;
wherein the conductive rod extends through the articulation joint and is configured to flex with the articulation joint during articulation of the joint.

3. The surgical device of claim 2, wherein the conductive rod is axially translatable when the articulation joint is articulated such that the first longitudinal axis of the elongate shaft intersects a second longitudinal axis of the end effector at a non-zero angle.

4. The surgical device of claim 1, wherein at least part of the conductive rod is configured to be exposed to tissue adjacent to the first jaw in the proximal-most, position such that energy can be applied to the tissue from the conductive rod in the proximal-most position.

5. The surgical device of claim 1, wherein the conductive rod has a conductive spring thereon that is slidably engageable with the electrode on the first jaw to allow energy to pass therebetween.

6. The surgical device of claim 1, wherein the conductive rod has a hook formed on a distal-most end thereof, and the first jaw is configured to receive the hook in a distal end thereof.

7. The surgical device of claim 6, wherein the hook of the conductive rod engages with the electrode on the first jaw to form the tissue-contacting surface on the first jaw in the proximal-most position.

8. The surgical device of claim 1, wherein the conductive rod comprises a cutting element.

* * * * *